(12) United States Patent
Wormsbecher

(10) Patent No.: US 7,166,213 B2
(45) Date of Patent: *Jan. 23, 2007

(54) SOLID COMPOSITIONS FOR SELECTIVE ADSORPTION FROM COMPLEX MIXTURES

(75) Inventor: Richard Franklin Wormsbecher, Dayton, MD (US)

(73) Assignee: W. R. Grace & Co.-Conn., Columbia, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/228,100

(22) Filed: Sep. 16, 2005

(65) Prior Publication Data

US 2006/0011549 A1 Jan. 19, 2006

Related U.S. Application Data

(62) Division of application No. 10/892,779, filed on Jul. 16, 2004, now Pat. No. 6,998,042, which is a division of application No. 09/929,621, filed on Aug. 14, 2001, now Pat. No. 6,802,966.

(51) Int. Cl.
*B01D 15/08* (2006.01)
(52) U.S. Cl. .............. 210/198.2; 210/635; 210/656; 210/502.1; 502/401
(58) Field of Classification Search ............ 210/635, 210/656, 198.2, 502.1; 502/400, 401, 403, 502/404
See application file for complete search history.

(56) References Cited

U.S. PATENT DOCUMENTS

| | | | | |
|---|---|---|---|---|
| 3,666,530 A | * | 5/1972 | Aue | ............ 428/429 |
| 3,669,841 A | | 6/1972 | Miller | ............ 195/63 |
| 3,715,278 A | | 2/1973 | Miller | ............ 195/63 |
| 3,795,313 A | * | 3/1974 | Kirkland et al. | ......... 210/198.2 |
| 3,873,426 A | | 3/1975 | Katchalski et al. | .......... 195/63 |
| 3,954,678 A | | 5/1976 | Marquisee | .......... 252/451 |
| 3,983,000 A | | 9/1976 | Messing et al. | ............. 195/63 |
| 3,983,299 A | * | 9/1976 | Regnier | .................... 428/405 |
| 4,029,583 A | * | 6/1977 | Ho Chang et al. | ......... 252/184 |

(Continued)

FOREIGN PATENT DOCUMENTS

EP 303406 2/1989

(Continued)

OTHER PUBLICATIONS

Greg T. Hermanson, A. Krishna Mallia, and Paul K. Smith, "Immobilized Affinity Ligand Techniques", (Academic Press. Inc., San Diego, CA, 1992) (TOC).

(Continued)

*Primary Examiner*—Ernest G. Therkorn
(74) *Attorney, Agent, or Firm*—William D. Bunch

(57) ABSTRACT

The present invention relates to a solid and method useful in separating chemical components in a complex mixture when at least one of the chemical components of the mixture is capable of being selectively adsorbed. The solid of the present invention comprises an inorganic substance and moieties ($R_{10}$) located on at least one surface of the inorganic substance, wherein said inorganic substance is an inorganic oxide and the surface moiety is selected from the group consisting of —$CH_2OH$, —$CH(OH)_2$, —$CH(OH)CH_3$, —$CH_2CH_2OH$, —$C(OH)_2CH_3$, —$CH_2CH(OH)_2$ and —$CH(OH)CH_2(OH)$. Binding moiety, optionally attached to the inorganic substance via a linker, can also be located on the surface of the solid.

8 Claims, 18 Drawing Sheets

U.S. PATENT DOCUMENTS

| | | | |
|---|---|---|---|
| 4,034,139 A | 7/1977 | Mazarguil et al. | 428/405 |
| 4,043,905 A * | 8/1977 | Novotny et al. | 210/198.2 |
| 4,177,038 A * | 12/1979 | Biebricher et al. | 8/192 |
| 4,206,259 A | 6/1980 | Rohrbach et al. | 428/304 |
| 4,258,133 A | 3/1981 | Mirabel et al. | 435/176 |
| 4,268,423 A | 5/1981 | Rohrbach et al. | 252/430 |
| 4,298,500 A * | 11/1981 | Abbott | 502/7 |
| 4,384,045 A | 5/1983 | Ho et al. | 435/176 |
| 4,415,663 A | 11/1983 | Symon et al. | 435/176 |
| 4,425,434 A | 1/1984 | Rosevear | 435/176 |
| 4,430,496 A | 2/1984 | Abbott | 536/27 |
| 4,469,630 A | 9/1984 | Flashner | 260/112 B |
| 4,520,122 A | 5/1985 | Arena | 502/152 |
| 4,540,486 A | 9/1985 | Ramsden | 210/198.2 |
| 4,544,485 A * | 10/1985 | Pinkerton et al. | 210/502.1 |
| 4,551,245 A | 11/1985 | Ramsden et al. | 210/198.2 |
| 4,606,825 A | 8/1986 | Crane et al. | 210/635 |
| 4,681,870 A | 7/1987 | Balint, Jr. et al. | 502/403 |
| 4,742,159 A | 5/1988 | Batz et al. | 530/388 |
| 4,778,600 A | 10/1988 | Williams | 210/198.2 |
| 4,828,695 A * | 5/1989 | Yamamura et al. | 210/198.2 |
| 4,837,348 A | 6/1989 | Stolowitz et al. | 556/9 |
| 4,918,016 A | 4/1990 | Leuba et al. | 435/176 |
| 4,925,818 A | 5/1990 | Schneider et al. | 502/7 |
| 4,994,429 A | 2/1991 | Wieserman et al. | 502/401 |
| 5,002,884 A | 3/1991 | Kobayashi et al. | 435/176 |
| 5,035,803 A | 7/1991 | Cohen | 210/656 |
| 5,043,062 A * | 8/1991 | Bale et al. | 210/198.2 |
| 5,045,190 A * | 9/1991 | Carbonell et al. | 210/198.2 |
| 5,055,194 A * | 10/1991 | Goetz et al. | 210/635 |
| 5,075,423 A | 12/1991 | Balint, Jr. | 530/350 |
| 5,077,210 A | 12/1991 | Eigler et al. | 435/176 |
| 5,085,779 A | 2/1992 | Crane et al. | 210/635 |
| 5,110,784 A * | 5/1992 | Williams et al. | 502/401 |
| 5,118,796 A | 6/1992 | Prior et al. | 530/388.1 |
| 5,137,627 A | 8/1992 | Feibush | 210/198.2 |
| 5,167,812 A * | 12/1992 | Graves et al. | 210/198.2 |
| 5,240,602 A | 8/1993 | Hammen | 210/198.2 |
| 5,277,813 A | 1/1994 | Feibush et al. | 210/502.1 |
| 5,362,859 A | 11/1994 | Zale | 530/413 |
| 5,371,262 A | 12/1994 | Arkles | 556/449 |
| 5,374,755 A | 12/1994 | Neue et al. | 556/400 |
| 5,403,750 A | 4/1995 | Braatz et al. | 436/531 |
| 5,405,766 A | 4/1995 | Kallury et al. | 435/174 |
| 5,431,807 A | 7/1995 | Frechet et al. | 210/198.2 |
| 5,527,711 A | 6/1996 | Tom-Moy et al. | 436/518 |
| 5,652,348 A | 7/1997 | Burton et al. | 536/20 |
| 5,663,051 A | 9/1997 | Vlasselaer | 435/7.23 |
| 5,667,674 A * | 9/1997 | Hanggi et al. | 210/198.2 |
| 5,667,692 A * | 9/1997 | Muller | 210/635 |
| 5,744,302 A | 4/1998 | Sessler et al. | 435/6 |
| 5,821,193 A | 10/1998 | Tani et al. | 502/401 |
| 5,876,595 A * | 3/1999 | Hanggi et al. | 210/198.2 |
| 5,945,520 A | 8/1999 | Burton et al. | 536/20 |
| 5,948,428 A | 9/1999 | Lee et al. | 424/426 |
| 5,993,653 A | 11/1999 | Ahmed et al. | 210/198.2 |
| 5,998,183 A | 12/1999 | Le Fevre et al. | 435/176 |
| 6,013,855 A | 1/2000 | McPherson et al. | 623/11 |
| 6,025,129 A | 2/2000 | Nova et al. | 435/6 |
| 6,045,697 A | 4/2000 | Girot et al. | 210/635 |
| 6,074,555 A * | 6/2000 | Boos et al. | 210/198.2 |
| 6,251,278 B1 | 6/2001 | Hammen | 210/635 |
| 6,375,846 B1 * | 4/2002 | Jarrett et al. | 210/635 |
| 6,987,079 B1 * | 1/2006 | Wormsbecher | 502/172 |
| 2003/0082658 A1 | 5/2003 | Mallet et al. | 435/7.92 |

FOREIGN PATENT DOCUMENTS

| | | |
|---|---|---|
| EP | 0 425 104 | 2/1991 |
| WO | WO 87/06586 | 11/1987 |
| WO | WO 98/31461 | 7/1998 |

OTHER PUBLICATIONS

Affinity Separations, A Practical Approach, Ed. Paul Matejtschuk: pp. 1-38.

ASTM D 5373—93 (Reapproved 1997)—"Standard Test Methods for Insrumental Determination of Carbon, Hydrogn, and Nitrogen in Laboratory Samples of Coal and Coke"; pp. 1-4.

ASTM D 5291-96; "Standard Test Methods for Instrumental Determination of Carbon, Hydrogen, and Nitrogen in Petroleum Products and Lubricants"; pp. 852-856.

Legrand, Andre P. "The Surface Properties of Silica," John Wiley & Sons, 1998, Chap. 3 & 4.

Chapman, Robert C. et al., J. Am. Chem. Soc 2000 122, 8303-8304—"Surveying for Surfaces that Resist the Adsorption of Proteins".

* cited by examiner

Chromatogram of Protein A Affinity Chromatography

Scheme 1

Scheme 2

Scheme 3

Scheme 4

Scheme 5

Scheme 6

Scheme 7

Scheme 8

Scheme 9

Scheme 10

SOLID COMPOSITIONS FOR SELECTIVE ADSORPTION FROM COMPLEX MIXTURES

CROSS REFERENCE TO RELATED CASES

This is a divisional application of Ser. No. 10/892,779 filed Jul. 16, 2004 now U.S. Pat. No. 6,998,042, which is a divisional application of Ser. No. 09/929,621, filed Aug. 14, 2001 now U.S. Pat. No. 6,802,966.

FIELD OF THE INVENTION

The present invention concerns solid compositions and methods useful in separating chemical components in a complex mixture in which at least one of the chemical components is capable of being selectively adsorbed. The invention also concerns methods of reducing non-specific binding of the other components in the mixture.

BACKGROUND OF THE INVENTION

Separations of components in a mixture have been important in many scientific disciplines, such as chemistry, biochemistry and molecular biology. The separation of components in a mixture allows isolation of the component of interest, i.e., an analyte. After the analyte is isolated, the properties of the analyte can be studied or used. Without the separation, it may be difficult to determine the properties of the analyte because, whatever the measurement technique used, the properties of the component of interest could be masked or influenced by other components in the mixture. Thus, separation techniques can be considered as corner stones in scientific studies.

The separation of components is made difficult if the mixture containing the analyte is a complex mixture. Good examples of complex mixtures include media of biological fermentation, cell cultures, transgenically produced milk, or slurries of transgenic plant matter, in which a specific analyte is desired and needs to be separated and purified. The separation of components in the complex mixture is usually accomplished by affinity separation techniques. The affinity separation technique usually involves contacting the mixture with a solid phase having a functionality specifically designed to bind to the analyte, but be substantially non-reactive with other components in the mixture, thereby leaving the other components free to be removed. After the non-bound components are removed, e.g. by washing the solid phase with water or buffer, the analyte is left behind bound to the solid phase, so the analyte is separated from the non-bound components. The analyte is then isolated by separating the analyte from the solid phase, usually by a buffer change, to recover the analyte as free molecules.

Classes of valuable "affinity" techniques for purification have been developed. These techniques have many names, affinity chromatography, affinity precipitation, immunoaffinity separation, etc., but they all rely on the same principles, that is, a specific functionality or binding moiety is chemically attached to a solid support that binds very selectively to the target analyte. The most common binding moieties for protein purification are other proteins such as Protein A or Protein G, or monoclonal antibodies, chelated metals ions, polypeptides, or small organic molecules. Monoclonal antibodies can be especially attractive for protein purification because they can be highly selective for the target protein. As indicated above, the mixture that contains the analyte is allowed to contact the affinity solid support with the binding moiety attached. The analyte binds to the binding moiety on the support and the rest of the mixture is removed. The analyte is then removed from the binding moiety by elution, usually achieved by changing the solvent. Very high purification factors can be realized. There is extensive literature on affinity techniques[1-8].

Recent developments in the selection and production of monoclonal antibodies have made the affinity technique based on the monoclonal antibody as the binding moiety a very powerful technique for the purification of proteins and biopharmaceuticals. Monoclonal antibodies are proteins themselves that are often purified from cell culture or fermentation using affinity purification that uses Protein A or Protein G as the ligand. New small organic Protein A mimetics have also been described as useful ligands for monclonal antibody purification.

Although affinity purification has proven to be a powerful technique, its full potential has not been fully realized. It is most commonly practiced where the support is formed into small beads, on the order of 0.05 to 0.5 mm or so, and the beads, often referred to as media, are loaded into a chromatography column. The mixture to be purified is then passed through the column and the analyte binds to the binding moiety attached to the media. The column is then washed extensively to remove the occluded mixture. An elution solvent is then passed through the column liberating the analyte in solution. On a large-scale, this process requires that the media have good physical strength to handle the weight and turbulence encountered in column applications.

Certain supports currently used in affinity separations, whether as column chromatography or some other system, are low surface area materials, such as carbohydrate-based materials or polymers. These low surface area supports can have low capacity. Because of the low capacity, relatively large loadings of media are needed to recover the target species. But, with large loadings of media, flow rates over the column are restricted to low rates due to pressure drop considerations. Column chromatography can also be practiced under high pressure where smaller beads are used to increase the capacity of the media. Because these beads must have higher strength to handle the pressure, carbohydrate gels are cross-linked, thereby lowering the capacity of the resulting beads. Therefore, there is a need to provide affinity supports with high capacity and which are further physically robust when used in high pressure liquid chromatography.

Developing high surface area supports is one approach to obtaining high capacity affinity separation media. With a higher capacity material, smaller amounts of the affinity support is needed to recover the target species, column pressure drops are lower, flow rates are higher, and there is less occluded feed contamination. High surface areas could range from 10–500 $m^2/g$. Materials that can provide high surface area are silica gels, silicas, aluminas, zirconias, carbohydrates, and polymeric materials such as macropore acrylic beads. In the case of silica gels, surface areas can vary from very low, 1 $m^2/g$, to very high, in excess of 800 $m^2/g$, with pore size modes from very low, less that 25 Å to in excess of 1500 Å. Furthermore, inorganic oxide-based materials are usually much more physically robust than the softer carbohydrate based supports.

When used as media in affinity separation techniques with a binding moiety attached, these oxide based materials, while having the requisite high surface area, can suffer from a high degree of non-selective binding of unwanted materials. Not all of the surface area will be used for the affinity separation; some will actually provide surface regions for non-selective adsorption. It is well known that proteins bind very strongly to silica for instance, sometimes irreversibly and non-selectively. Therefore, while the binding moiety can be very selective, the unused regions of the surface will be non-selective. The net effect is to lower the selectivity of the high surface area materials, thereby reducing the purification factors of the overall process. This non-selective adsorption by many oxide supports, and especially silicas such as silica gels, is the reason these materials are currently not used extensively as affinity separation supports.

One of the objectives of this invention to describe a surface composition to be applied to high surface area materials which improve the non-selective adsorption while retaining the high capacity for the selective affinity binding.

Such compositions will have great value in "affinity separations" from complex biological mixtures where specific biological species, such as proteins, are synthesized by genetically engineered organisms. For instance the complex mixture might be a fermentation broth for cellular or bacterial production of a target protein. The fermentation broths are complex mixtures of proteins, carbohydrates, etc., that support the organism growth, as well as by products produced by the fermentation. The target species can also be produced from the fermentation and is produced by the organism into the broth. In some cases, the target species is produced in the cell. Recovery is therefore complicated by the fact the cells need to be homogenized and the target dissolved. These mixtures are particularly insidious for target species isolation and purification. Separation and purification schemes for the isolation and purification of the target species from fermentation broths are very complicated and expensive. The cost of isolation and purification is especially significant as the large-scale production. Because of the challenging nature of this problem, the field of purification and isolation is extensive.

SUMMARY OF THE INVENTION

The solid composition of the invention comprises an inorganic substance and moiety $R_{10}$ located on at least one surface of said inorganic substance, wherein
said inorganic substance is an inorganic oxide
and said $R_{10}$ group is an entity selected from the group consisting of —$CH_2OH$, —$CH(OH)_2$, —$CH(OH)CH_3$, —$CH_2CH_2OH$, —$C(OH)_2CH_3$, —$CH_2CH(OH)_2$ and —$CH(OH)CH_2(OH)$.

When $R_{10}$ is an entity selected from the group consisting of —$CH_2OH$, —$CH(OH)_2$, —$CH(OH)CH_3$, —$CH_2CH_2OH$, —$C(OH)_2CH_3$, —$CH_2CH(OH)_2$ and —$CH(OH)CH_2(OH)$, the solid support possesses a distinctive characteristic of having reduced non-specific binding of any non-analyte components in a complex mixture. The members of $R_{10}$ have a common property of having zero electric charge and being hydrophilic. Without being held to any particular theory, it is believed that when the solid support has any of the $R_{10}$ entities, i.e. —$CH_2OH$, —$CH(OH)_2$, —$CH(OH)CH_3$, —$CH_2CH_2OH$, —$C(OH)_2CH_3$, —$CH_2CH(OH)_2$ and —$CH(OH)CH_2(OH)$, located on its surface, the binding of the non-analyte component in the mixture to the surface has an entropy change lower than the remaining non-analyte component in the mixture's aqueous phase. Binding of any component, e.g., non-analyte or analyte component, from a solution to a surface involves a lowering of entropy due to localization of the non-analyte on the surface. In order for binding to be favorable, there has to be an interaction between non-analyte and surface, such as a Columbic charge interaction or hydrophobic interaction, to overcome the lowering of entropy due to surface localization. Coating with any one of or any mixture of the entities for $R_{10}$, however, produces a hydrophilic surface, as well as a surface having a zero net charge which reduces interaction necessary for reducing entropy and accordingly reduces non-binding of non-analyte.

Also within the scope of the present invention are solids comprising the inorganic substance, moiety $R_{10}$ located on at least one surface of the inorganic substance and at least one binding moiety capable of binding analyte. The moiety $R_{10}$ is preferably located on a portion of the inorganic oxide's surface and on the remainder of the surface is located binding moiety. The binding moiety is selected to provide bonding to a particular analyte and provides the highly selective binding for affinity separations, while the surface coated with $R_{10}$ groups reduces non-selective binding of other species. In preferred embodiments, a significant, if not a large majority, of the inorganic oxide surface is covered by $R_{10}$ groups, e.g., at concentrations of about 1 to 10 groups per $nm^2$ substrate, and the remainder covered by the binding moiety.

Also within the scope of the invention is a solid comprising the inorganic substance in which binding moiety is optionally located on the inorganic oxide surface through a linker. The linker can be located on the inorganic oxide surface by reacting a linker compound with the inorganic oxide and then subsequently reacting the linker with the binding moiety. Accordingly, the invention contemplates inorganic substances comprising linker groups and $R_{10}$ moieties located on its surface. This solid in turn can be transferred to an end user who can attach a specifically designed binding moiety to the linker for use in a separation.

DETAILED DESCRIPTION OF THE INVENTION

Inorganic Substance

Figure 1:
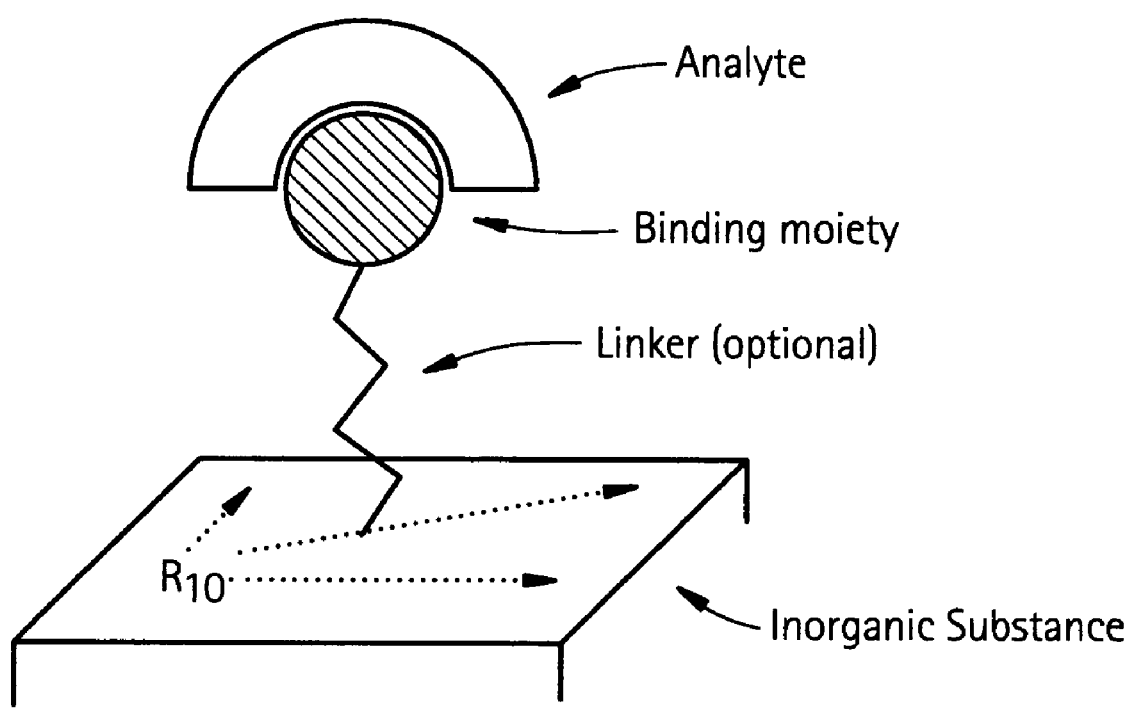
FIG. 1 schematically depicts the composition of this invention comprising the inorganic substance, $R_{10}$ surface moieties, the optional linker, binding moiety and analyte.

Inorganic substances suitable for making the invention include those products commercially available as chromatographic media. These substances can be prepared using methods known in the art. The inorganic substance can also be considered a support for the binding moiety later described below and from time to time the inorganic substance is referred to herein as a "support." In general, the inorganic substance of the present invention is an inorganic oxide, more suitably an inorganic metal oxide, silicate or aluminosilicate. Inorganic metal oxide is preferred. Inorganic oxides suitable for this invention have free hydroxyl groups capable of bonding to or reacting with other chemical functionalities. It is through those hydroxyl groups that $R_{10}$ surface moieties and binding moieties and/or linkers are reacted or bonded. In general, suitable inorganic oxides include those having about 1 to about 10 hydroxyl groups per square nanometer of solid inorganic oxide.

Examples of the preferred inorganic metal oxide include silica such as chromatographic grade silica or silica gel, alumina, silica-alumina, zirconia, zirconate, controlled pore glass or titania. The inorganic metal oxide preferably is silica, more preferably chromatographic grade silica or silica gel. Magnetically responsive inorganic metal oxides, such as siliceous oxide-coated magnetic particles disclosed in WO 98/31461 (the disclosure of which is incorporated by reference) are also suitable. Mixed inorganic metal oxides, e.g. cogels of silica and alumina, or coprecipitates can also be used. Solids prepared from sodium silicate are examples of a suitable silicate and zeolite is an example of a suitable aluminaosilicate. The solid of the present invention can be in a physical form of particulates, fibers and plates.

Surface Moieties ($R_{10}$)

As indicated earlier, $R_{10}$ groups are selected from the group consisting of —$CH_2OH$, —$CH(OH)_2$, —$CH(OH)CH_3$, —$CH_2CH_2OH$, —$C(OH)_2CH_3$, —$CH_2CH(OH)_2$ and —$CH(OH)CH_2(OH)$. $R_{10}$ preferably is an entity selected from the group of —$CH_2OH$, —$CH(OH)CH_3$, —$CH_2CH_2OH$, and —$CH(OH)CH_2(OH)$. More preferably, $R_{10}$ is an entity selected from the group of —$CH_2OH$, —$CH(OH)CH_3$ and —$CH_2CH_2OH$. Most preferably $R_{10}$ is —$CH_2OH$.

The moiety $R_{10}$ is located on at least one surface of the inorganic substance. By "located" it is meant $R_{10}$ can be attached directly to a functionality on the surface of the starting inorganic substance. $R_{10}$ can be located on surface area present on the periphery of the inorganic substance, or located on surface area presented in pores which penetrate into the interior of the inorganic substance and have (pore) openings on the substance's periphery.

$R_{10}$ can also be "located" on the surface of the inorganic substance by being attached to the inorganic substance surface via bivalent moiety or atom (—X—) to form a group having the formula —X—$R_{10}$. The bivalent moiety or atom linking $R_{10}$ in this embodiment is not present in the composition of the starting inorganic substance prior to reaction of the substance with the reactant. The moiety or atom can be from a reactant employed to create $R_{10}$, e.g., a residual metal atom (e.g. silicon atom), originating from a silane reactant. The residual moiety or atom is attached directly to said inorganic substance, and preferably through hydroxyl groups on the surface of the inorganic substances. The —X— group in such reactants vary from reactant to reactant, but can be metal atoms or other chemical moieties. For example, X can be derived from metal atoms such as silicon, aluminum, zirconium or the like. The inorganic substance selected may also determine the selection of —X— and its associated reactant. Generally, any reactant containing —X— will be that which can react with reactive functionality on the inorganic substance. In the case of inorganic oxides, suitable reactants typically are those capable of reacting with hydroxyl groups.

The chemistry of reacting compounds, e.g., those capable of creating $R_{10}$, with the inorganic substances is known in the art, e.g., Smith, *Organic Synthesis*, John Wiley & Sons, 1994; March, *Advanced Organic Chemistry*, John Wiley & Sons, Fourth Edition, 1992; Larock, *Comprehensive Organic Transformations*, John Wiley & Sons, Second Edition, 1999; Greene et al, *Protective Groups in Organic Synthesis*, John Wiley & Sons, Third Edition, 1999; Brook, *Silicon in Organic, Organometallic, and Polymer Chemistry*, John Wiley & Sons, 2000; Hermanson et al, *Immobilized Affinity Ligand Techniques,* 1992; Weetall, "Covalent Coupling Methods for Inorganic Support Materials", in *Methods in Enzymology*, vol. XLIV, edited by K. Mosbach, pp. 134–148, 1976; Abbott, U.S. Pat. No. 4,298,500; and Arkles, U.S. Pat. No. 5,371,262; the disclosures of these documents are herein incorporated by reference. For example, a solid comprising $R_{10}$ groups located on the inorganic substance's surface can be prepared from a reactant or coating agent such as alkoxysilane, dialkoxysilane or trialkoxysilane bearing a precursor group of $R_{10}$. For instance, acetoxymethyl can be the precursor group of hydroxymethyl. The coating agent is then allowed to react with the surface of the inorganic substance, followed by hydrolysis of the precursor to produce an inorganic substance having $R_{10}$ groups attached.

Figure 13:
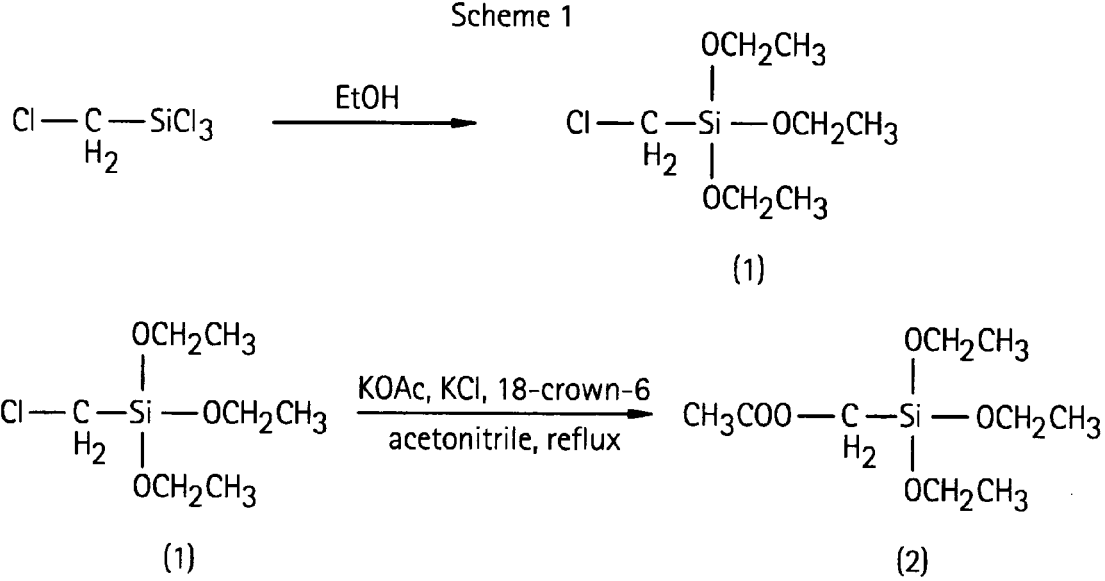
FIG. 13 depicts the preparation of a coating agent that yields —$CH_2OH$ as $R_{10}$, from reaction illustrated in FIG. 14.
Figure 14:
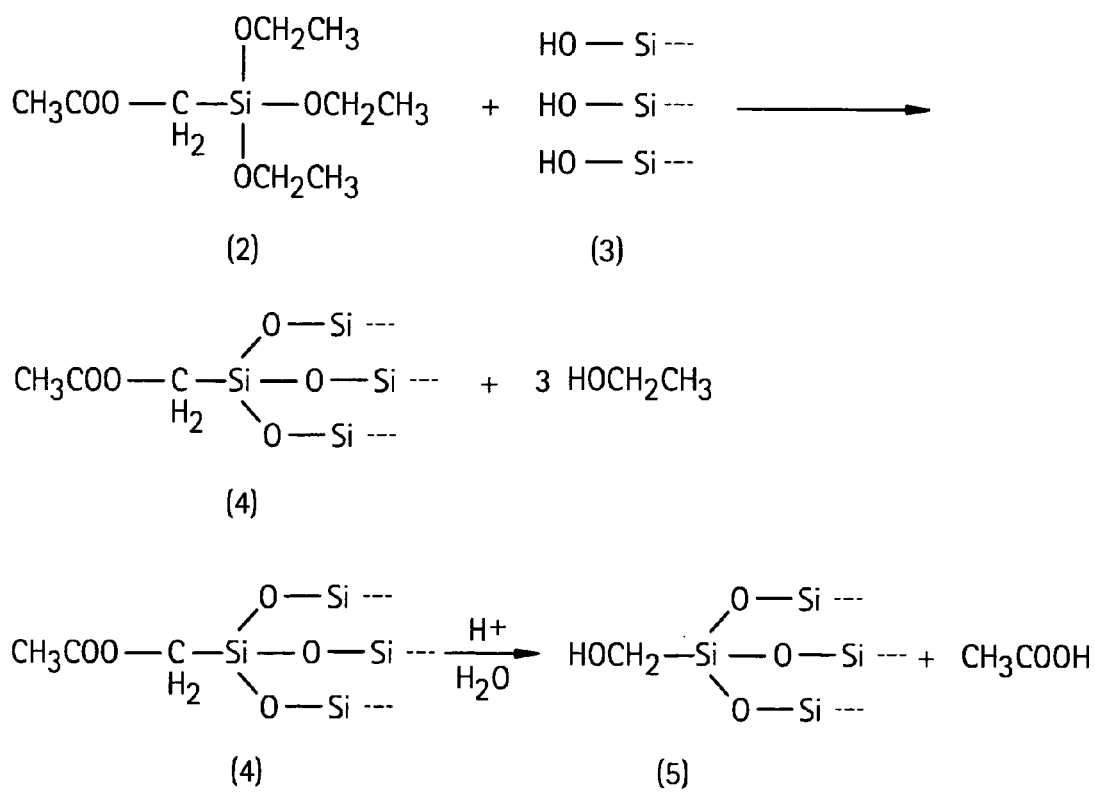
FIG. 14 shows the preparation of silica having $R_{10}$ attached via a silicon atom which is not a part of the silica, in which $R_{10}$ is —$CH_2OH$, so that —Si—$CH_2OH$ is directly attached to the silica (HO—Si— represents a silanol group on the surface of silica).

A method for preparing silica having —$CH_2OH$ as $R_{10}$ located on the silica surface is shown in FIGS. 13 and 14. FIG. 13 depicts the preparation of a coating agent, acetoxymethyltriethoxysilane (see Compound (2)), for introducing Si—$R_{10}$ groups to silanol groups at the surface of silica, i.e. HO—Si—, in which $R_{10}$ is hydroxymethyl (see the reactions presented in FIG. 14, in which Compound (5) is silica having Si—$R_{10}$ directly attached at the surface wherein $R_{10}$ is hydroxymethyl). In other words, in FIG. 14, a method is shown for introducing $R_{10}$ groups to the surface of silica via a Si atom which is an example of the residual moiety or atom X described above as being residual from the reactant and which is not a part of the starting inorganic substance.

Figure 15:
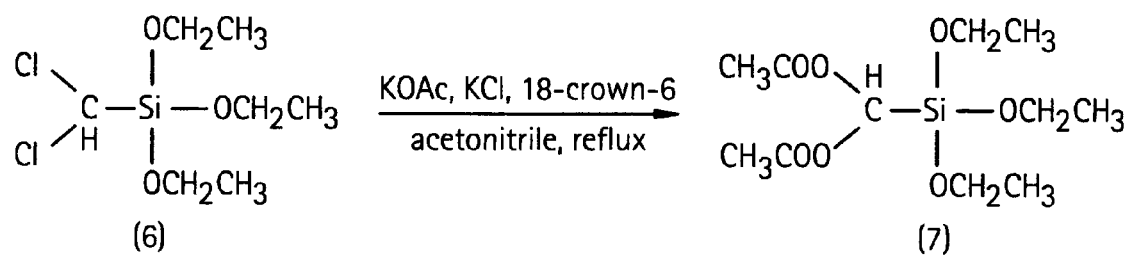
FIG. 15 depicts the preparation of a coating agent that yields —$CH(OH)_2$ as $R_{10}$, from reaction illustrated in FIG. 16.
Figure 16:
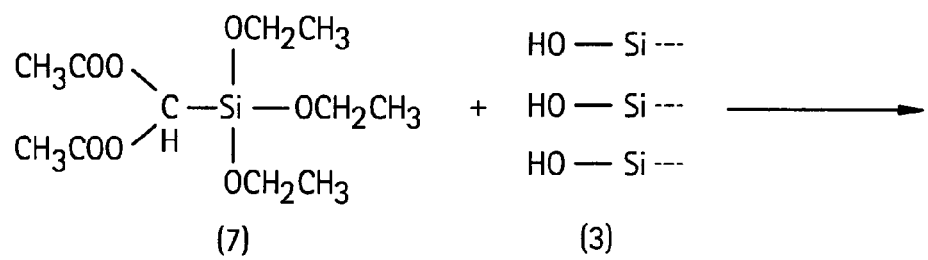
FIG. 16 shows the preparation of silica having $R_{10}$ indirectly attached via a silicon atom which is not a part of the silica, so that —Si—$R_{10}$ groups are attached to the silica's surface, in which $R_{10}$ is —$CH(OH)_2$(HO—Si— represents a silanol group on the surface of silica).
Figure 16:
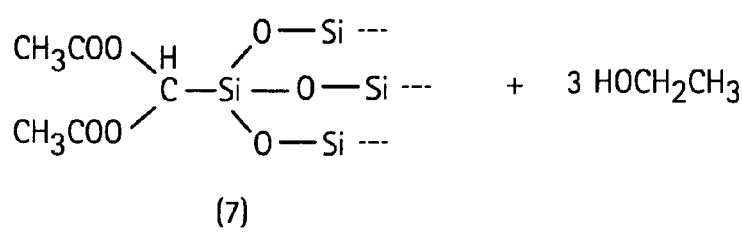
Figure 16:
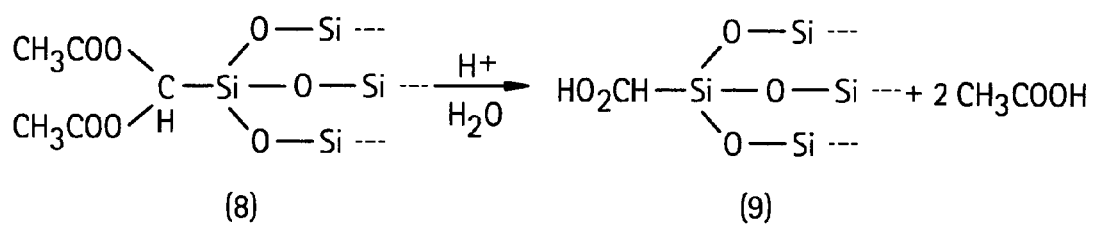

A method for the preparing silica comprising $R_{10}$, wherein $R_{10}$ is —$CH(OH)_2$ is shown in FIGS. 15 and 16. FIG. 15 depicts the preparation of a coating agent, diacetoxymethyltriethoxysilane (see Compound (7)), for introducing —$CH(OH)_2$ groups as the $R_{10}$ group to the surface of silica (see the reactions and Compound (9) presented in FIG. 16).

Figure 17:
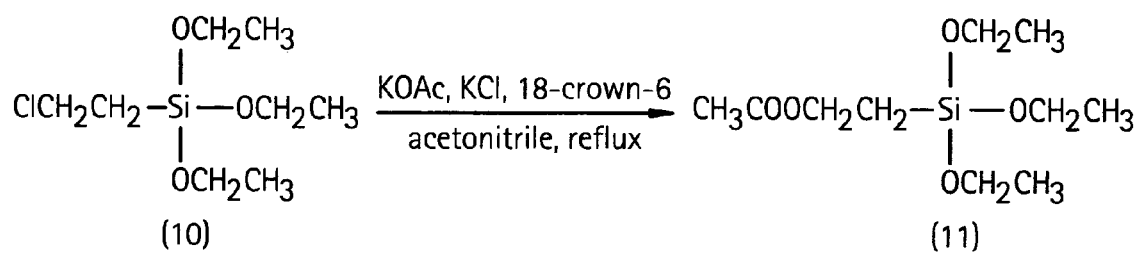
FIG. 17 shows the preparation of a coating agent that yields hydroxyethyl as $R_{10}$, from reaction illustrated in FIG. 18.

FIG. 17 shows a method for preparing a coating agent, acetoxyethyltriethoxysilane (see Compound (11)), for introducing 2-hydroxyethyl to the surface of silica.

Figure 18:
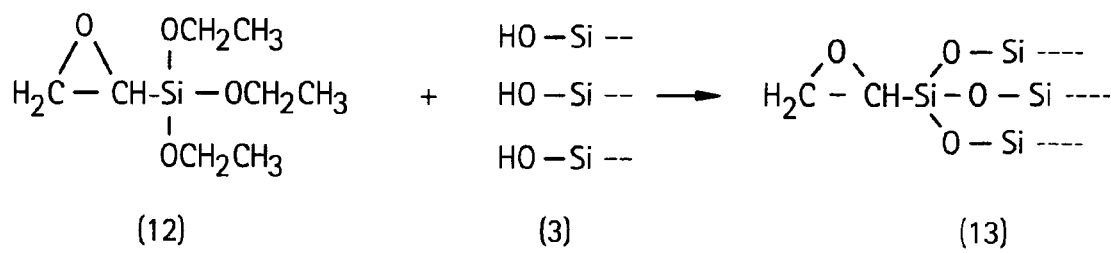
FIG. 18 shows a method for the preparation of a solid comprising silica and —Si—$R_{10}$ groups attached to the surface of the silica, i.e. $R_{10}$ is indirectly attached via a silicon atom which is not a part of the silica to the silica surface, wherein $R_{10}$ is 1,2-dihydroxyethyl.
Figure 18:
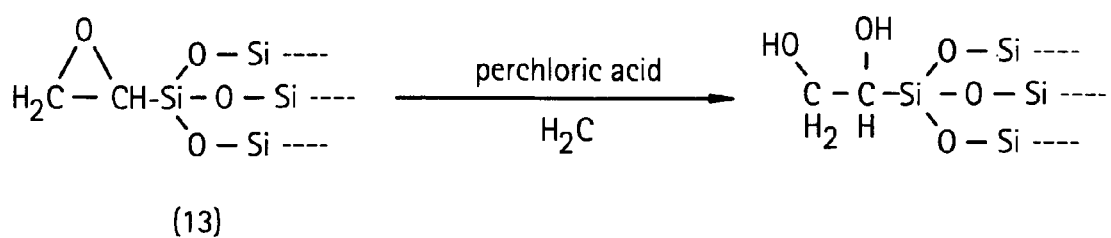
Figure 19:
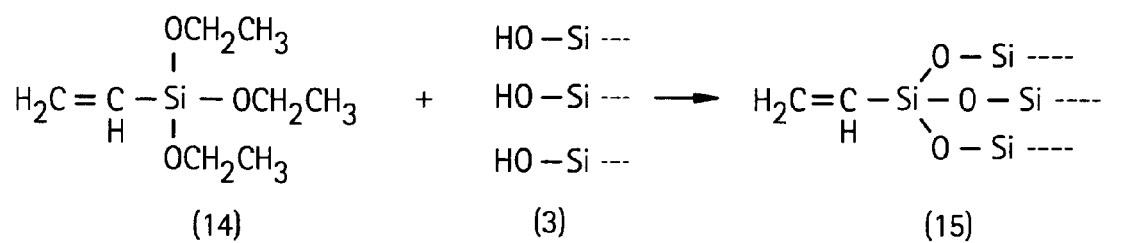
FIG. 19 shows another method for preparing a solid comprising silica and —Si—$R_{10}$ groups attached to the surface of the silica, i.e. $R_{10}$ is indirectly attached via a silicon atom which is not a part of the silica to the silica surface, wherein $R_{10}$ is 1,2-dihydroxyethyl.
Figure 19:
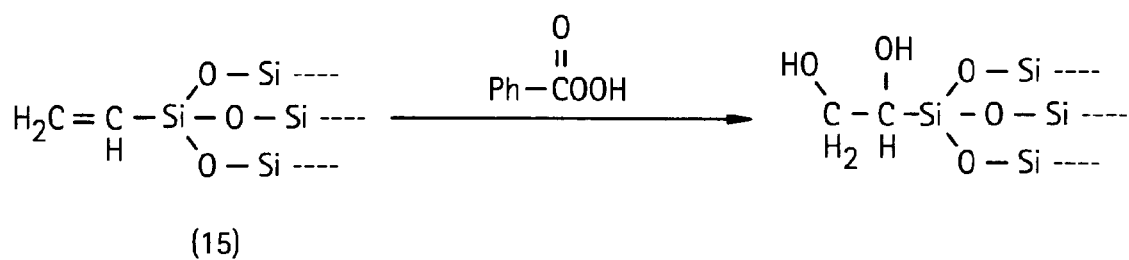
Figure 20:
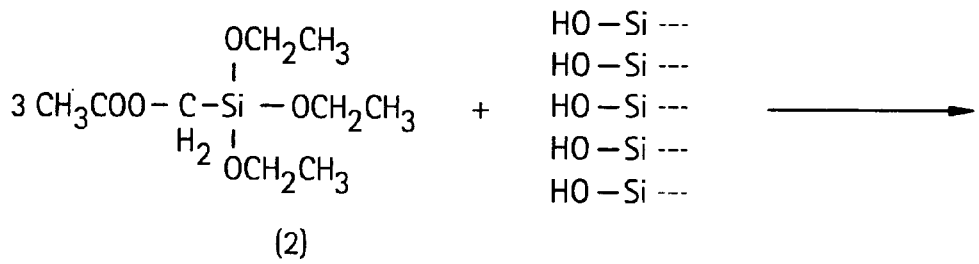
FIG. 20 shows an embodiment of the present invention in which —Si—$R_{10}$ groups are crosslinked when attached to the surface of silica, wherein $R_{10}$ is hydroxymethyl (HO—Si— represents a silanol group on the surface of silica).
Figure 20:
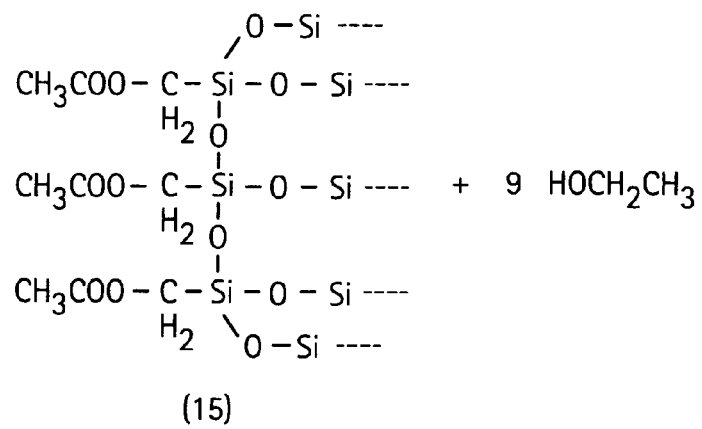
Figure 20:
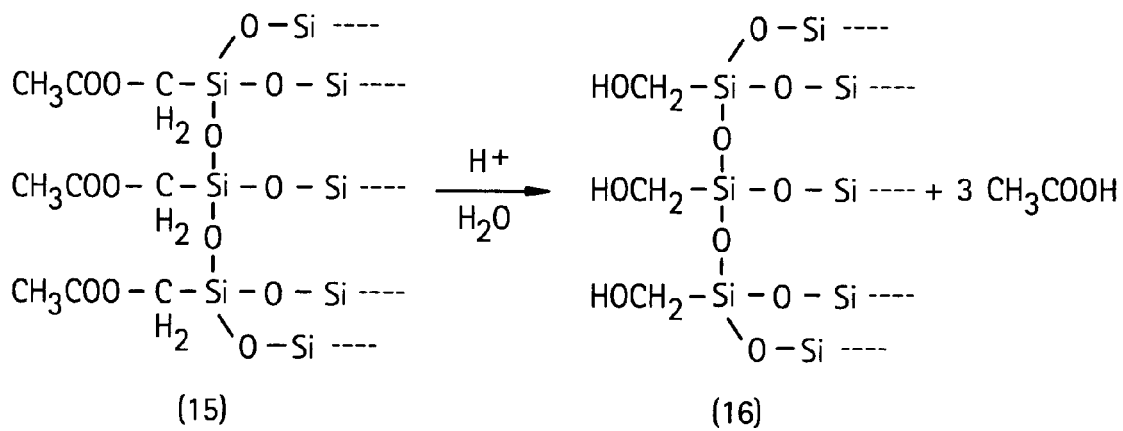

Two methods for the preparation of a solid comprising silica and 1,2-dihydroxyethyl as $R_{10}$ groups attached to the surface of the silica are depicted in FIGS. 18 and 19.

Also, within the scope of the present invention are solids comprising the inorganic substance having $R_{10}$ groups attached to a surface of the solid via a residual metal (e.g., Si) from the silane reactant wherein each resulting Si—$R_{10}$ group is attached to the inorganic substance via three covalent bonds (e.g. see the final products of the reaction schemes in FIGS. 14, 16, 18 and 19, resulting from the reaction of a coating agent having three silanol groups).

Figure 21:
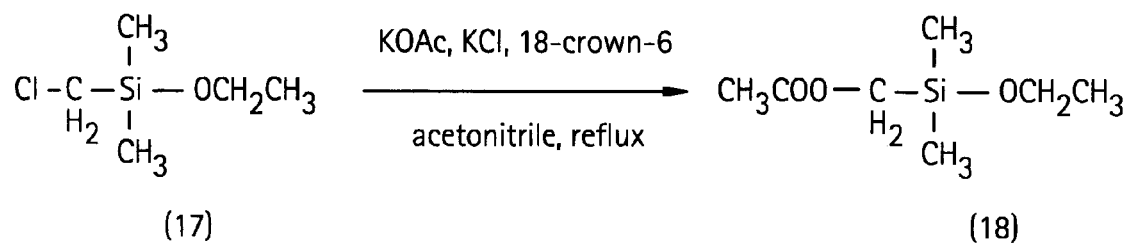
FIG. 21 shows the preparation of a coating agent that would lead to the —Si—$R_{10}$ group attaching to the surface of silica at a single point, wherein $R_{10}$ is hydroxymethyl, resulting from the reaction illustrated in FIG. 22.
Figure 22:
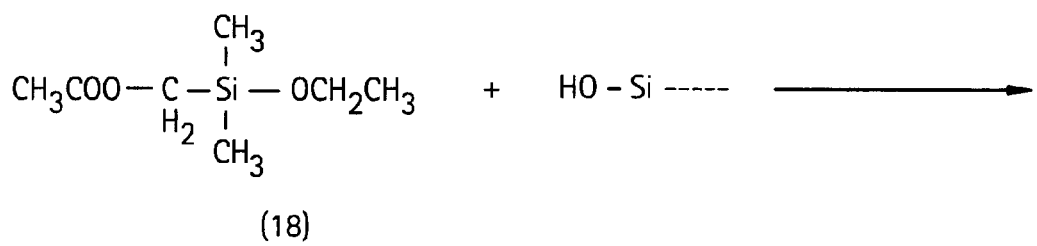
FIG. 22 depicts an embodiment of the present invention in which the —Si—$R_{10}$ group is attached to the surface of silica at a single point, wherein $R_{10}$ is hydroxymethyl (HO—Si— represents a silanol group on the surface of silica).
Figure 22:
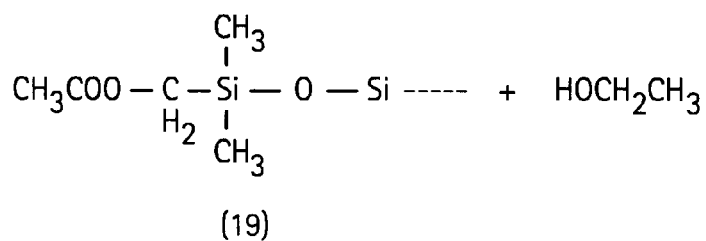
Figure 22:
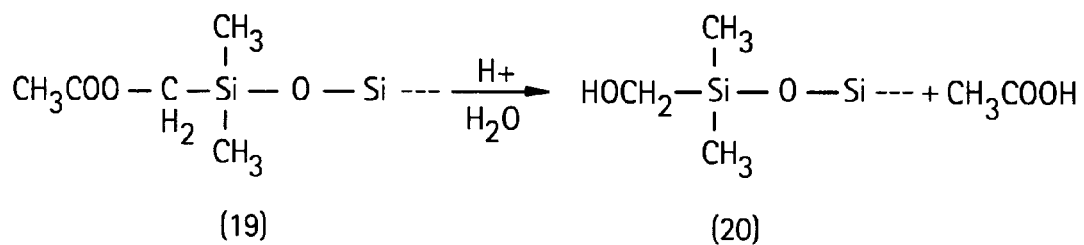

As seen in FIGS. 21 and 22, it is also believed coating agents can be selected so that residual atoms can also be attached to the inorganic substance via one or two covalent bonds, or that certain embodiments comprise crosslinking of the Si atoms. Such crosslinking can be a Si—O—Si linkage or another linkage such as Si—O—C(O)—O—Si, Si—O-alkylene-O—Si or Si—O—C(O)-alkylene-O—Si). The final product, i.e. Compound (20), of the reaction scheme in FIG. 22 illustrates an embodiment of the solid of the present invention in which Si—$R_{10}$ group has a single point of attachment to the surface of the silica. That embodiment is prepared from a reaction of the solid inorganic substance and mono-ethoxysilane (see FIG. 21 for the preparation of the coating agent which is a mono-ethoxysilane).

Binding Moiety

The solid of the present invention can further comprise at least one binding moiety which is attached to, optionally via a linker, or otherwise located on the surface of said inorganic substance. The binding moiety is any molecule or molecule fragment capable of binding to another moiety or molecule-based analyte, e.g., binding through hydrophobic interaction, covalent bonding or Columbic interaction. Such moieties are well known to those skilled in the separations industry. Moieties typically used in the bioseparations industry include (e.g. biotin, avidin and streptavidin), natural or unnatural protein, peptide, antigen and nucleic acid. As the binding moiety of the solid of the present invention, the protein is preferably a receptor or antibody.

It is also preferred that, in the solid of the present invention, the binding moiety is ligand, a receptor, antibody, antigen, DNA or RNA, including hybridization probes for nucleic acids. When the ligand is avidin or streptavidin, the analyte can be biotin or biotinylated, and vice versa.

The binding moiety is attached to the inorganic substance using methods known in the art (e.g. Hermanson et al, *Immobilized Affinity Ligand Techniques*, Academic Press, 1992 and the other references cited earlier with respect to attaching $R_{10}$ moieties). In solids comprising inorganic oxides, the binding moiety can be attached via a reaction with surface functional groups, e.g., hydroxyl, on the starting inorganic oxide.

Alternatively, the binding moiety can be attached to the inorganic substance via a linker. The linker can be a bivalent chemical group, which is optionally substituted. The optionally substituted bivalent chemical group can comprise n —R— groups, with n being the number of —R— groups, n being an integer of at least 1, preferably not larger than 30, and more preferably not higher than 15. More typically, the bivalent chemical group is about 1 to about 30 atoms, preferably about 1 to about 20 atoms, more preferably about 5 to about 15 atoms, in length measured from the binding moiety to the inorganic substance. The chemical group —R— can be selected from the group consisting of —$C(R_1)$H—, —$C(R_2)$=$C(R_3)$— and —C≡C—, where $R_1$, $R_2$ and $R_3$ independently being H, alkyl, substituted alkyl, cycloalkyl, substituted cycloalkyl, alkenyl, substituted alkenyl, cycloalkenyl, substituted cycloalkenyl, alkynyl, substituted alkynyl, cycloalkynyl, substituted cycloalkynyl, aryl, substituted aryl, aralkyl or substituted aralkyl, said —R— group optionally replaced with —O—, —S—, carbonyl, thiocarbonyl, —OC(O)—, —C(O)O—, —SC(O)—, —C(O)S—, —OC(S)—, —C(S)O—, —C(S)S—, —SC(S)—, —$N(R_4)$—, —$N(R_4)C(O)$—, —$C(O)N(R_4)$—, —$C(R_5)$=N—, —N=$C(R_5)$—, —$C(R_5)$=NO—, —ON=$C(R_5)$—, —P—, —P(OH)O—, arylene, substituted arylene, cycloalkylene, substituted cycloalkylene, cycloalkenylene, substituted cycloalkenylene, bivalent heterocyclyl or bivalent substituted heterocyclyl, where $R_4$ and $R_5$ independently being H, alkyl, substituted alkyl, cycloalkyl, substituted cycloalkyl, alkenyl, substituted alkenyl, cycloalkenyl, substituted cycloalkenyl, alkynyl, substituted alkynyl, cycloalkynyl, substituted cycloalkynyl, aryl, substituted aryl, aralkyl or substituted aralkyl. Illustrative of the chemical group is "hydrocarbyl" comprising n —R— groups and wherein n is described above, at least one —R— group is —$CH_2$— and (n−1) —R— groups are optionally replaced with the R groups mentioned above, e.g., —O—, —S—, etc.

"Substituted" is used herein to mean containing pendent substituent groups that do not alter the predominant chemical character of the substituted R group, e.g., hydrocarbon character for hydrocarbyls.

The term "alkyl" refers to a saturated branched or unbranched hydrocarbyl radical, preferably those of 1 to 30, more preferably 1 to 20 and even more preferably 1 to 6, carbon atoms. Examples of "alkyl" include methyl, ethyl, n-propyl, isopropyl, n-butyl, sec-butyl, isobutyl, tert-butyl, n-pentyl, 1-methylbutyl, 2-methylbutyl, isopentyl, neopentyl, 1,1-dimethylpropyl, n-hexyl, 1-methylpentyl, 2-methylpentyl, 3-methylpentyl, 1,1-dimethylbutyl, 2,2-dimethylbutyl, isohexyl and neohexyl. The term "cycloalkyl" refers to a saturated cyclic hydrocarbyl radical, preferably of 3 to 10, and more preferably 3 to 6, carbon atoms. Examples of "cycloalkyl" include cyclopropyl, cyclobutyl, cyclopentyl, cyclohexyl, bicycloheptyl and decalin. "Alkenyl" is a branched or unbranched hydrocarbyl radical having at least one C=C bond, wherein the hydrocarbyl radical is preferably of 2 to 30, more preferably 2 to 20 and even more preferably 2 to 6, carbon atoms. Examples of "alkenyl" include vinyl, allyl, 1-propenyl, isopropenyl, 2-butenyl, 1,3-butadienyl, 3-pentenyl and 2-hexenyl. "Cycloalkenyl" refers to a cyclic hydrocarbyl radical, preferably of 3 to 10, preferably 3 to 6, carbon atoms having at least one C=C bond. "Alkynyl" is a branched or unbranched hydrocarbyl radical, preferably of 2 to 30, more preferably 2 to 20 and even more preferably 2 to 6, carbon atoms having at least one —C≡C— bond. Examples of "alkynyl" include ethynyl, 1-propynyl, 2-propynyl, 2-butynyl, 3-butynyl and 2-penten-4-ynyl. "Cycloalkynyl" is a cyclic hydrocarbyl radical preferably of 3 to 10, more preferably 3 to 6, carbon atoms having at least one —C≡C— bond. Examples of "cycloalkynyl" include pentynyl and hexynyl. "Aryl" is an aromatic cyclic hydrocarbyl radical, preferably of 6 to 14 carbon atoms. Examples of "aryl" include phenyl, naphthyl, anthracyl and phenanthryl, with phenyl being the preferred aryl. "Aralkyl" is an alkyl radical substituted with one or more aryl radical.

Examples of "aralkyl" include benzyl, phenethyl, diphenylmethy and trityl, with benzyl being the preferred aralkyl. "Bivalent heterocyclyl" are bivalent cyclic radicals typically having 3 to 10, preferably 3 to 7, more preferably 4 to 6, ring atoms with 1 to 4 of the ring atoms being O, S or N atoms, or mixture of O, S and/or N atoms. Examples of bivalent heterocyclyl include bivalent radicals of thiirene, oxirane, aziridine, 1H-azirine, 2H-azirine, 2H-thiete, thietane, 2H-oxete, oxetane, azete, azetidine, 1,2-oxazetidine, thiophene, furan, pyrrole, imidazole, oxazole, isoxazole, thiazole, isothiazole, pyrazole, 1,3-dioxolane, 1,2,3-thiadiazole, 1,3,4-thiadiazole, 1,2,4-thiadiazole, 1,2,3-oxadiazole, 1,2,4-oxadiazole, 1,3,4-oxadiazole, 1,2,5-oxadiazole, 1,2,3-triazole, 1,2,4-triazole, tetrazole, oxadiazole, pyridine, quinoline, isoquinoline, quinolizine, quinazoline, pteridine, carbazole, benzoxazole, 1,3-oxazine, 2H-1,3-oxazine, phenazine, phenothiazine, pyridazine, pyrimidine, pyrazine, benzo[b]furan, benzo[b]thiophene, indole, isoindole, indazole, purine, isobenzofuran, tetrahydrofuran, 1,4-dioxane, pyrrolidine, tetrahydropyran, 1,2-dihydropyridine, 1,4-dihydropyridine, piperidine, piperazine, morpholine, thiomorpholine, chroman, isochroman, chromene, 1H-azepine, 3H-azepine, 1,2-diazepine, 1,3-diazepine, 1,4-diazepine, triazepines and azocine. "Heteroaryl" refers to aromatic heterocyclic radicals. "Alkylene", "alkenylene", "alkynylene", "cycloalkylene", "cyclalkenylene" and "arylene" are bivalent equivalents of the alky, alkenyl, alkynyl, cycloalkyl, cycloalkenyl and aryl radicals, respectively.

"Substituted alkyl" is an alkyl substituted with 1 to 5, preferably 1 to 3, substituents selected from the group consisting of hydroxy, sulfydryl, alkoxy, alkylthio, amino, alkylamino, dialkylamino, arylamino, N,N-arylalkylamino, diarylamino, azido, amidino, ureido, fluoro, chloro, bromo, iodo, nitro, cyano, acyl (preferably acetyl and benzoyl), thioacyl, alkylsulfinyl, alkylsulfonyl, alkylsulfonamido, alkylsulfamoyl, carboxyl, alkylcarbonyloxy (preferably acetoxy), arylcarbonyloxy (preferably benzoyloxy), alkoxycarbonyloxy, aryloxycarbonyloxy, carbamoyl, aryl (preferably phenyl), styryl, cycloalkyl, cycloalkenyl and heterocyclyl (preferably heteroaryl).

"Substituted alkenyl" is an alkenyl substituted with 1 to 5, preferably 1 to 3, substituents selected from the group consisting of hydroxy, sulfydryl, alkoxy, alkylthio, amino, alkylamino, dialkylamino, arylamino, N,N-arylalkylamino, diarylamino, azido, amidino, ureido, fluoro, chloro, bromo, iodo, nitro, cyano, acyl (preferably acetyl and benzoyl), thioacyl, alkylsulfinyl, alkylsulfonyl, alkylsulfonamido, alkylsulfamoyl, carboxyl, alkylcarbonyloxy (preferably acetoxy), arylcarbonyloxy (preferably benzoyloxy), alkoxycarbonyloxy, aryloxycarbonyloxy, carbamoyl, aryl (preferably phenyl), styryl, cycloalkyl, cycloalkenyl and heterocyclyl (preferably heteroaryl).

"Substituted alkynyl" is an alkynyl substituted with 1 to 5, preferably 1 to 3, substituents selected from the group consisting of hydroxy, sulfydryl, alkoxy, alkylthio, amino, alkylamino, dialkylamino, arylamino, N,N-arylalkylamino, diarylamino, azido, amidino, ureido, fluoro, chloro, bromo, iodo, nitro, cyano, acyl (preferably acetyl and benzoyl), thioacyl, alkylsulfinyl, alkylsulfonyl, alkylsulfonamido, alkylsulfamoyl, carboxyl, alkylcarbonyloxy (preferably acetoxy), arylcarbonyloxy (preferably benzoyloxy), alkoxycarbonyloxy, aryloxycarbonyloxy, carbamoyl, aryl (preferably phenyl), styryl, cycloalkyl, cycloalkenyl and heterocyclyl (preferably heteroaryl).

"Substituted cycloalkyl" is a cycloalkyl substituted with 1 to 5, preferably 1 to 3, substituents selected from the group consisting of alkyl, alkenyl, alkynyl, aralkyl, hydroxy, sulfydryl, alkoxy, alkylthio, amino, alkylamino, dialkylamino, arylamino, N,N-arylalkylamino, diarylamino, azido, amidino, ureido, fluoro, chloro, bromo, iodo, nitro, cyano, acyl (preferably acetyl and benzoyl), thioacyl, alkylsulfinyl, alkylsulfonyl, alkylsulfonamido, alkylsulfamoyl, carboxyl, alkylcarbonyloxy (preferably acetoxy), arylcarbonyloxy (preferably benzoyloxy), alkoxycarbonyloxy, aryloxycarbonyloxy, carbamoyl, aryl (preferably phenyl), styryl, cycloalkyl, cycloalkenyl and heterocyclyl (preferably heteroaryl).

"Substituted cycloalkenyl" is a cycloalkenyl substituted with 1 to 5, preferably 1 to 3, substituents selected from the group consisting of alkyl, alkenyl, alkynyl, aralkyl, hydroxy, sulfydryl, alkoxy, alkylthio, amino, alkylamino, dialkylamino, arylamino, N,N-arylalkylamino, diarylamino, azido, amidino, ureido, fluoro, chloro, bromo, iodo, nitro, cyano, acyl (preferably acetyl and benzoyl), thioacyl, alkylsulfinyl, alkylsulfonyl, alkylsulfonamido, alkylsulfamoyl, carboxyl, alkylcarbonyloxy (preferably acetoxy), arylcarbonyloxy (preferably benzoyloxy), alkoxycarbonyloxy, aryloxycarbonyloxy, carbamoyl, aryl (preferably phenyl), styryl, cycloalkyl, cycloalkenyl and heterocyclyl (preferably heteroaryl).

"Substituted cycloalkynyl" is a cycloalkynyl substituted with 1 to 5, preferably 1 to 3, substituents selected from the group consisting of alkyl, alkenyl, alkynyl, aralkyl, hydroxy, sulfydryl, alkoxy, alkylthio, amino, alkylamino, dialkylamino, arylamino, N,N-arylalkylamino, diarylamino, azido, amidino, ureido, fluoro, chloro, bromo, iodo, nitro, cyano, acyl (preferably acetyl and benzoyl), thioacyl, alkylsulfinyl, alkylsulfonyl, alkylsulfonamido, alkylsulfamoyl, carboxyl, alkylcarbonyloxy (preferably acetoxy), arylcarbonyloxy (preferably benzoyloxy), alkoxycarbonyloxy, aryloxycarbonyloxy, carbamoyl, aryl (preferably phenyl), styryl, cycloalkyl, cycloalkenyl and heterocyclyl (preferably heteroaryl).

"Substituted aryl" is an aryl substituted with 1 to 5, preferably 1 to 3, substituents selected from the group consisting of alkyl, alkenyl, alkynyl, aralkyl, hydroxy, sulfydryl, alkoxy, alkylthio, amino, alkylamino, dialkylamino, arylamino, N,N-arylalkylamino, diarylamino, azido, amidino, ureido, fluoro, chloro, bromo, iodo, nitro, cyano, acyl (preferably acetyl and benzoyl), thioacyl, alkylsulfinyl, alkylsulfonyl, alkylsulfonamido, alkylsulfamoyl, carboxyl, alkylcarbonyloxy (preferably acetoxy), arylcarbonyloxy (preferably benzoyloxy), alkoxycarbonyloxy, aryloxycarbonyloxy, carbamoyl, styryl, cycloalkyl, cycloalkenyl, aryl (preferably phenyl) and heterocyclyl (preferably heteroaryl).

"Substituted heterocyclyl" is a heterocyclyl radical substituted with 1 to 5, preferably 1 to 3, substituents selected from the group consisting of alkyl, alkenyl, alkynyl, aralkyl, hydroxy, sulfydryl, alkoxy, alkylthio, amino, alkylamino, dialkylamino, arylamino, N,N-arylalkylamino, diarylamino, azido, amidino, ureido, fluoro, chloro, bromo, iodo, nitro, cyano, acyl (preferably acetyl and benzoyl), thioacyl, alkylsulfinyl, alkylsulfonyl, alkylsulfonamido, alkylsulfamoyl, carboxyl, alkylcarbonyloxy (preferably acetoxy), arylcarbonyloxy (preferably benzoyloxy), alkoxycarbonyloxy, aryloxycarbonyloxy, carbamoyl, aryl (preferably phenyl), styryl, cycloalkyl, cycloalkenyl and heterocyclyl (preferably heteroaryl).

"Substituted arylene", "substituted cycloalkylene", "substituted cycloalkenylene", "substituted bivalent heterocyclyl" and "substituted aralkyl" are bivalent equivalents of "substituted aryl", "substituted cycloalkyl", "substituted cycloalkenyl" and "substituted heterocyclyl".

The linkage connecting the chemical group —R— of the linker and inorganic substance depends on the chemistry employed to react the linker and inorganic substance. The linkage can be an ether, thioether, ester, thioester, carbonate, carbamate, phosphate, phosphonate, phosphoester, phosphoramidate, amine, amide, imide, urea, thiourea, sulfonamide, sulfoxide, sulfone, disulfide, oxime, O-acyl oxime, O-carbamoyl oxime, O-acyloxyalkyl oxime, O-acyloxyalkyloxy oxime, O-oximinophosphate, O-oximinophosphonate, O-oximinophosphoramidate or —C=C-linkage. The linkage connecting the chemical group —R— and binding moiety can also be one of the aforementioned linkages.

The chemistry of reacting linkers to substances (e.g., inorganic substances) is well described in the literature (see Hermanson et al, *Immobilized Affinity Ligand Techniques*, 1992 and Weetall, *Methods in Enzymology*, vol. XLIV, pp. 134–148, 1976). The particular chemistry for reacting linker to inorganic substances depends on the inorganic substance and linker employed. Likewise, the chemistry of reacting the linker to binding moiety depends on the linker and binding moiety employed. Specific examples of suitable linker/binding moiety coupling chemistry are shown in Table 1. According to Table 1, the binding moiety can be coupled to the linker via an amino, sulfhydryl, carbonyl or hydroxy group or an active hydrogen atom on the binding moiety.

TABLE 1

Examples of Conventional Linker/Binding Moiety Coupling Chemistry

| Linkers Formed With | Binding Moiety Coupling Group |
|---|---|
| Cyanogen bromide (CNBr) | Amino |
| N-Hydroxy succinimide esters | Amino |
| Carbonyl diimidazole | Amino |
| Reductive amination | Amino |
| FMP activation* | Amino |
| EDC-mediated amide bond formation** | Amino |
| Organic sulfonyl chlorides: tosyl chloride and tresyl chloride | Amino |
| Divinylsulfone | Amino |
| Azlactone | Amino |
| Cyanuric chloride (trichloro-s-triazine) | Amino |
| Iodoacetyl or bromoacetyl activation methods | Sulfhydryl |
| Maleimide | Sulfhydryl |
| Pyridyl disulfide | Sulfhydryl |
| Divinylsulfone | Sulfhydryl |
| Epoxy | Sulfhydryl |
| TNB-Thiol*** | Sulfhydryl |
| Hydrazide | Carbonyl |
| Reductive amination | Carbonyl |
| Epoxy (bisoxirane) | Hydroxy |
| Divinylsulfone | Hydroxy |
| Cyanuric chloride | Hydroxy |
| Diazonium compounds | Active hydrogen |
| Mannich condensation | Active hydrogen |

*FMP means 2-fluoro-1-methyl-pyridinium toluene-4-sulfonate
**EDC means 1-ethyl-3-(3-dimethylaminopropyl) carbodiimide
***TNB-thiol means 2-iminothiolane 5,5-dithio-bis-(2-nitrobenzoic acid)

In making solid supports comprising linker groups, the order of creating linker groups in conjunction with adding $R_{10}$ groups to the inorganic substance can vary. The $R_{10}$ can be created on the inorganic surface after attaching the linker, or it can be created prior to reacting linker. Alternatively, precursors to either $R_{10}$ or the linker or both can be created and/or attached, with the precursors later reacted to create the final $R_{10}$ and/or linker.

The concentration of linker groups on the inorganic surface can vary. In certain embodiments of the present invention, the binding moiety comprises large protein molecules which can "shadow" large regions of the support's surface area. As a result, the concentration of the linker sites on the support's surface does not need to be relatively high. The concentration can be optimized based on the size of the contemplated binding moiety/analyte complex.

Factors that determine concentrations of $R_{10}$ and binding moiety include the identity of $R_{10}$ group and binding moiety, concentration of reactive sites on the inorganic substance, concentration of linker groups, and identity of analyte.

In general, the concentration of $R_{10}$ can be in the range of about 1 to about 10 groups per square nanometer ($nm^2$) of support surface area, based on surface area measured by BET. In certain embodiments, the binding moiety concentration depends primarily on the analyte sought to be recovered when using the composition. As indicated above, the concentration of binding moiety can also depend on the concentration of any optional linker used. In general, however, the binding moiety can be in a concentration in the range of 0.04 to about 4 groups per square nanometer. In addition, binding moiety is not always attached to a linker on a one to one stoichiometry. In certain embodiments, e.g., when the binding moiety is prepared from a large protein molecule, the binding moiety can be attached by several linker groups. In other embodiments employing smaller binder moieties, less than stoichiometric amounts of binding moieties are used and any unreacted linker groups are "capped" to avoid interference when the invention is used for a separation.

The amount of $R_{10}$ and binding moiety can also be stated in terms of how many functional groups on the starting inorganic substance are reacted or "covered" by the $R_{10}$, binding moiety, and/or or optional linker. For example, about 50% to about 99% of surface hydroxy groups of said inorganic substance can be covered with the $R_{10}$ surface moieties and about 1% to about 50% of the surface hydroxy groups can be covered with the binding moiety, optionally attached to the inorganic substance via the linker.

In certain embodiments of the solid of the present invention, about 75% to about 99% of the surface hydroxy groups of said inorganic substance is covered with the $R_{10}$ surface moieties and about 1% to about 25% of the surface hydroxy groups is covered with the binding moiety directly or indirectly attached to the inorganic substance via the linker.

As indicated above, the solid of this invention comprising at least one binding moiety and $R_{10}$ can be employed to isolate analytes known to bind to the binding moiety. Accordingly, the present invention encompasses a method of isolating an analyte mixed with at least one other component in a mixture, said method comprising the following steps:
1. contacting a solid of the present invention with said mixture, wherein the at least one binding moiety has a specific affinity for said analyte;
2. allowing said analyte to bind to said at least one binding moiety;
3. removing said at least one other component from the solid said analyte bound thereto;
4. recovering the solid; and
5. isolating the analyte from the solid.

In an embodiment of the method of the present invention, the binding moiety is present in an amount sufficient to provide specific binding to a desired analyte. The at least one other component is removed in step (3) by washing the solid with a fluid and discarding the washate; and wherein said analyte is isolated in step (5) by placing an eluant on the solid and collecting the eluant.

In the method of isolating the analyte, it is preferred that about 50% to about 99% of the hydroxy groups of a surface of said inorganic substance is covered with the surface moieties and about 1% to about 50% of the hydroxy groups of the surface is covered with the binding moiety directly or indirectly attached to the inorganic substance via the linker.

The method of isolating the analyte further prefers that about 75% to about 99% of the hydroxy groups of the surface of said inorganic substance is covered with the surface moieties and about 1% to about 25% of the hydroxy groups of the surface is covered with the binding moiety directly or indirectly attached to the inorganic substance via the linker.

In a preferred embodiment of the method of isolating the analyte, said inorganic substance is a silica gel or chromatographic grade silica. More preferably the inorganic substance is silica gel.

The present invention also includes a method of reducing nonspecific binding of impurity (impurities are non-analyte components, i.e. species other than the analyte, in a mixture containing the analyte) to a solid comprising an inorganic substance, wherein said inorganic substance comprises at least one functional group to which non-specific binding occurs or which otherwise causes non-specific binding. The inorganic substance comprises the aforementioned inorganic oxide and the method comprises the following steps:
1. providing said solid;
2. reacting said at least one functional group with reactant to create moiety $R_{10}$ on at least one surface of the inorganic substance, wherein $R_{10}$ is selected from the group consisting of —$CH_2OH$, —$CH(OH)_2$, —$CH(OH)CH_3$, —$CH_2CH_2OH$, —$C(OH)_2CH_3$, —$CH_2CH(OH)_2$ and —$CH(OH)CH_2(OH)$.

In the method of reducing non-specific binding, $R_{10}$ is preferably an entity selected from the group consisting of —$CH_2OH$, —$CH(OH)CH_3$, —$CH_2CH_2OH$, and —$CH(OH)CH_2(OH)$. More preferably, $R_{10}$ is an entity selected from the group consisting of —$CH_2OH$, —$CH(OH)CH_3$ and —$CH_2CH_2OH$. Most preferably, $R_{10}$ is —$CH_2OH$. $R_{10}$ is present on the surface of the inorganic substance in sufficient amounts such that when the inorganic substance is contacted with a mixture comprising impurity, non-specific binding of the impurity to the solid is reduced.

The method is particularly useful in reducing non-specific binding to inorganic metal oxides, silicates or aluminosilicate having hydroxyl functionality located on its surface. It is particularly useful for inorganic metal oxides such as silica (silica gel and chromatographic grade silica), alumina, silica-alumina, zirconia, zirconate, controlled pore glass, titania, coprecipitates and mixtures thereof. The method is also useful on magnetically responsive inorganic oxides (such as siliceous oxide-coated magnetic particles).

There are three types of binding of proteins or other species to the support surface that must be considered to minimize the non-selective binding to the solid support.

The surface charge of the support should be ideally zero at the operating pH of the adsorption. This is due to the fact that proteins carry a net charge due to the excess of —COOH or —$NH_2$ groups in the protein. For a complex mixture of proteins at about pH 7, if a protein in the mixture has an isoelectric point <7 it will have a net negative charge, and conversely if a protein in the mixture has an isoelectric point >7 it will have a net positive charge. An unreacted silica surface has an isoelectric point of about 2, so if it is contacted with a complex mixture at pH=7 or so, it will have a strong negative charge, and therefore the proteins that are positively charge will adsorb non-selectively to the silica surface. This explains the strong non-selective binding of proteins to silica surfaces. Therefore, as stated above, the surface charge of the support should be ideally zero at the operating pH of the adsorption.

The second type of binding interaction that should be minimized is hydrophobic bonding. Although weaker than electrostatic or dipole interactions at single sites, hydrophobic interactions become appreciable when it becomes collective between many adjacent sites. The hydrophobic interaction becomes dominant when the salt concentration of the solvent is relatively high. The ions of the salt can interact with the charged surface, thereby "screening the charge" from the proteins. While the presence of high salt reduces the electrostatic interaction with the surface, hydrophobic interactions become dominant, if the surface has a hydrophobic character. Therefore, a hydrophobic surface composition should be avoided on the support to minimize this interaction.

The third type of binding interaction of proteins to surfaces is hydrogen bonding, or a dipolar interaction. Interestingly, if the solvent is water, this interaction will favor the solvent over the surface due to entropy considerations. That is, if a protein has a "choice" to bind to a surface through hydrogen bonding or, remain in solution in the water system, which is also a hydrogen bonding interaction, the solution case is favored because of its higher entropy state. Therefore, for protein purification from aqueous solution, a surface that has a dipolar composition is favored to minimize non-selective binding. Such a surface is typically hydrophilic at low electrostatic charge density.

It is believed that the invention addresses each of these three interactions and that one of the novel features of this invention is a surface composition that presents a hydrophilic surface with very low surface charge density for protein purification from water based systems. This surface composition is achieved by chemically modifying inorganic oxide based support, such as silica, preferably silica gels with the aforementioned $R_{10}$ groups such as —$CH_2OH$, —$CH(OH)_2$, —$CH(OH)CH_3$, —$CH_2CH_2OH$, —$C(OH)_2CH_3$, —$CH_2CH(OH)_2$ and —$CH(OH)CH_2(OH)$, preferably —$CH_2OH$, covering the surface. These $R_{10}$ groups are hydrophilic yet are very weak acids, meaning that these $R_{10}$ groups are essentially not disassociated at pH less than about 12 or so, and therefore are not charged. When a complex mixture of proteins are presented with this surface composition, charge interactions are minimized, yet hydrogen bonding interactions will favor the hydrogen bonding from the water solvent due to higher entropy state of the solvated protein over a protein hydrogen bonded to the surface. This surface composition will then minimize non-selective binding of unwanted proteins to the high capacity affinity support, yielding high purification factors at high capacity.

Also in the scope of the invention are solids comprising $R_{10}$ moieties and at least one linker located on a surface of the inorganic substance. Such solids can be considered an intermediate which can be sold "as is" to a user of the solid. Prior to isolating a desired analyte, the user can then react a binding moiety to the linker group. The linker groups may also optionally be capped or otherwise in a precursor form which would require further chemistry before reacting it with a binding moiety.

The following working examples are presented to illustrate some of the aspects of the present invention and should not be construed to limit the scope of the present invention. The present invention may be embodied in embodiments not illustrated by the Examples without departing from the spirit or essential attributes of the invention disclosed herein. For instance, the present invention can be practiced by one skilled in the art as described in the claims and any embodiments having elements equivalent to elements recited in the claims are included within the scope of the claimed invention.

EXAMPLES 1 AND 2

Non-Specific Binding on Conventional Silica Media

These examples show that the neat uncoated charged silica surface of the prior art strongly adsorbs proteins based mostly on isoelectric point and the surface area of the silica. Two types of silicas were tested: Examples 1 and 2. Example 1 was a low surface area silica gel with a surface area=161 m$^2$/g after 4 hours at 150° C. heat treat (micropore=73 m$^2$/g; mesopore=88 m$^2$/g, pore volume=0.373 cc/g, average pore diameter=93 Å). Example 2 was a higher surface area/pore volume silica gel, surface area=253 m$^2$/g after 4 hours at 150° C. heat treat (micropore=35 m$^2$/g; mesopore=218 m$^2$/g, pore volume=2.445 cc/g, average pore diameter=387 Å). The examples below describe a procedure where the neat silica samples were contacted with a complex mixture of proteins in aqueous solution. The resultant supernatant was then analyzed by isoelectric focussing gel electrophoresis for protein adsorption.

A vial (325 µg protein/vial) of Pharmacia 3.6-9.3 Broad pI Calibration Kit (catalog # 17-0471-01) was dissolved in 200 µl DI H$_2$O in an eppendorf tube. 0.005 g of Example 1 was added. In another eppendorf tube, a vial (325 µg protein/vial) of Pharmacia 3.6-9.3 Broad pI Calibration Kit (catalog # 17-0471-01) was dissolved in 200 µl DI H$_2$O and then 0.005 g of Example 2 was added. Both samples were stirred end over end for 1 hour. These samples were run subjected to 3-9 Isoelectric Focussing Gel Electrophoresis on a Pharmacia PhastGel unit. The results are shown in FIG. 2.

| Lane | Description |
|------|-------------|
| 2, 7 | Pharmacia 3.6–9.3 Broad pI Standard |
| 3, 4 | Example 1 |
| 5, 6 | Example 2 |

Figure 2:
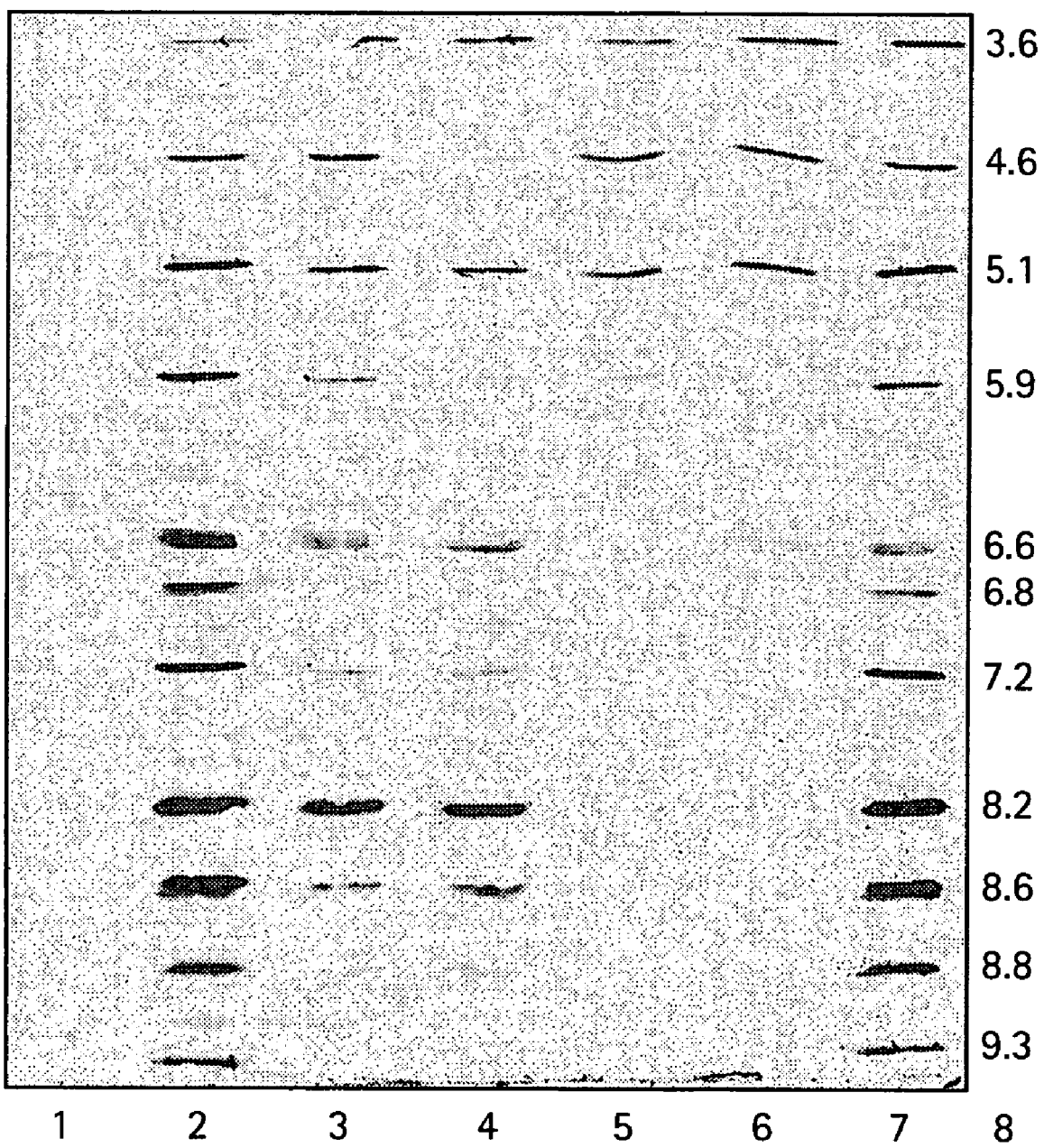
FIG. 2 shows the results of Examples 1 and 2, with lanes 2 and 7 representing Pharmacia 3.6-9.3 Broad pI Standard, lanes 3 and 4 representing Example 1 and lanes 5 and 6 representing Example 2. This figure illustrates non-specific binding of untreated conventional inorganic oxides.

FIG. 2 shows that bands (proteins) were missing from the samples that were contacted with Examples 1 and 2, which means that these proteins adsorbed to the silica surfaces. The high surface area silica, Example 2, adsorbed all of the proteins with isoelectric points greater than 5.9, while the lower surface silica, Example 1 adsorbed only proteins of higher pI. The data clearly show that uncoated silica binds proteins primarily through a strong electrostatic interaction, and that the surface is negatively charged at this pH (assumed to be around 5.5 or so).

EXAMPLES 3, 4, AND 5

Non-Selective Binding on Hydrophobic Treated Supports

These examples show that when the silica is coated with hydrophobic groups, methyl or octyl groups, strong adsorption occurs, especially at moderate ions strength of the solvent, ~0.1 M salt. Example 3 was an uncoated neat commercial wide pore silica from W. R. Grace & Co., XWP-gel P 005, SA=72 m$^2$/g, with 50 nm pore median that had been activated for 2 hours at 150° C. Example 4 was the silica of Example 3 that had been coated with methyl groups, described below. Example 5 was the silica of Example 3 that had been coated with octyl groups, described below. Example 4 was prepared as follows. In a 250 ml round bottom flask, 50 ml toluene and 6.16 g of methyltriethoxysilane were added. Then 10.1 g of Example 3 was added to a toluene/methyltriethoxysilane solution. N$_2$ was flowed for 5 minutes to remove air and continued for the entire reaction. The sample was refluxed and stirred at 110° C. for 4 hours. The sample was then filtered and washed 3 times with 50 ml of toluene. The sample was reslurried into 50 ml of toluene, then filtered and washed 3 times with 50 ml of toluene. The sample was then reslurried into 50 ml of toluene, filtered and washed 3 times with 50 ml of toluene. The sample was dried at 110° C. and then calcined 4 hours at 150° C.

Example 5 was prepared as follows. 10.1 g of Example 3 was impregnated to incipient wetness with 0.53 g of octyltriethoxysilane dissolved in 13.25 g of toluene as solvent. The sample was then air-dried in a hood for 2 hours, dried at 110° C. for one hour and then calcined 4 hours at 150° C.

Protein adsorption in 0.1 M NaCl was determined as follows. Because Examples 4 and 5 were hydrophobic, a wetting procedure was needed to insure good contact with the protein solution. To an eppendorf tube, 0.014 g Example 3 was added as the control. Then 1 ml ethanol was added, stirred and centrifuged with a supernatant removed. 0.5 ml ethanol and 0.5 ml DI H$_2$O were added, stirred and centrifuged with a supernatant removed. 0.25 ml ethanol and 0.75 ml DI H$_2$O were added, stirred and centrifuged with a supernatant removed. 1 ml DI H$_2$O was added, stirred and centrifuged with a supernatant removed. The DI H$_2$O wash was repeated four more times. 1 ml 0.1 M NaCl+0.02 M PBS pH=7.4 were added, stirred and centrifuged with a supernatant removed. The wash with 0.1 M NaCl+0.02 M PBS pH=7.4 was repeated four more times. Two vials of Sigma IEF Mix 3.6-9.3 Isoelectric Focusing Marker (catalog # I-3018) were dissolved into 500 µl 0.1 M NaCl+0.02 M PBS pH=7.4. The dissolved IEF Mix was added to an eppendorf tube.

To another eppendorf tube, 0.014 g of Example 4 was added. The same wetting procedure and protein addition as Example 3 were performed with Example 4.

To a third eppendorf tube, 0.014 g of Example 5 was added. The same wetting procedure and protein addition as Example 3 were performed with Example 5.

One vial of Sigma IEF Mix 3.6-9.3 Isoelectric Focusing Marker (catalog # I-3018) was dissolved into 250 µl 0.1 M NaCl+0.02 M PBS pH=7.4. This was the standard untreated protein mixture.

All samples were stirred end over end for 1 hour. The samples were subjected to 3-9 Isoelectric Focussing Gel Electrophoresis on a Pharmacia PhastGel unit. The results are shown in FIG. 3.

| Lane | Description |
|------|-------------|
| 1, 8 | Standard protein mixture |
| 2, 3 | Example 3 |
| 4, 5 | Example 4 |
| 6, 7 | Example 5 |

Figure 3:
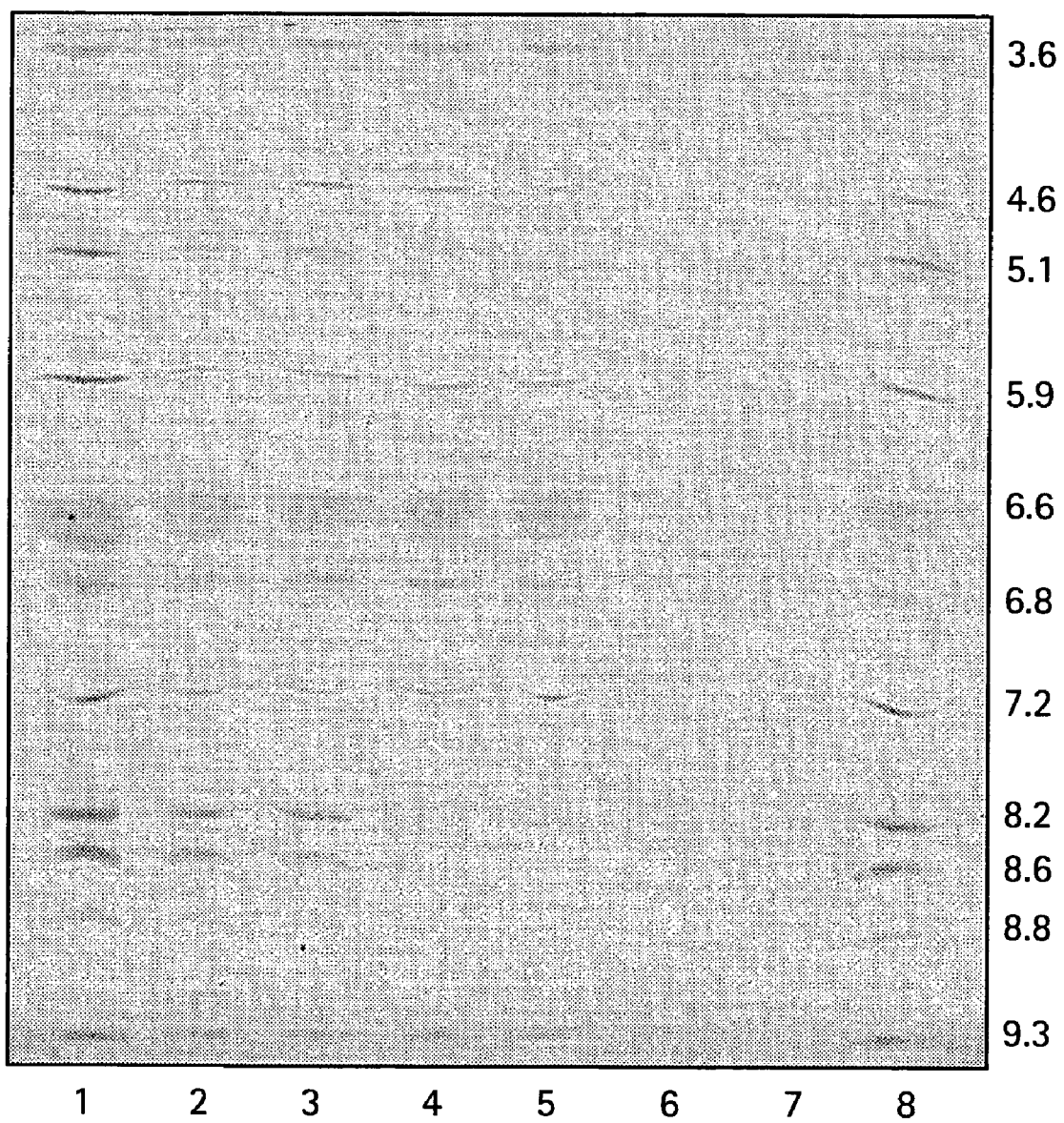
FIG. 3 shows the results of Examples 3–5.

As seen in FIG. 3, while the surface charge of the silica was "screened" by the dissolved salt, 0.1M NaCl, and no protein binding occurred, the hydrophobic interaction of the methyl, and especially the octyl, groups was very strong and many of the bands were missing. These data show clearly that at the conditions above, a hydrophobic surface composition can lead to non-selective binding.

EXAMPLES 6, 7 AND 8

Example of Invention

These Examples show the advantage of employing an $R_{10}$ group according to this invention for reducing non-selective protein binding to a silica surface. Example 6 was the same as Example 3 except it was activated 2 hours at 200° C. Example 7 was an intermediate surface composition, with the silica surface having Si—R groups attached, wherein R is acetoxymethyl. Example 8 was an example of the surface composition of the present invention, with the silica surface having Si—$R_{10}$ groups attached, wherein $R_{10}$ is methylhydroxy. The advantage of Example 8 with high and low ionic strength solvents was also shown.

Example 7 was prepared as follows. In a 250 ml round bottom flask, 50 ml toluene and 20.42 g of acteoxymethyltriethoxysilane were added. 15.05 g of Example 6 was added to a toluene/acteoxymethyltriethoxysilane solution. $N_2$ was flowed for 5 minutes to remove air and continued for the entire reaction. The sample was refluxed and stirred at 110° C. for 16 hours. Then, the sample was filtered and washed 3 times with 50 ml of toluene. The sample was reslurried into 50 ml of toluene, filtered and washed 5 times with 50 ml of toluene. The sample was then reslurried into 50 ml of toluene, filtered and washed 5 times with 50 ml of toluene. It was dried at 110° C. then calcined 4 hours at 150° C.

The preparation of Example 8 is described as follows. In a 250 ml round bottom flask, 10 g of Example 7 and 100 ml 0.01 M $H_2SO_4$ were added. $N_2$ was flowed for 5 minutes to remove air and continued for entire reaction. The sample was refluxed and stirred at 100° C. for 18 hours. Then, the sample was filtered and washed 2 times with 100 ml 80° C. DI $H_2O$. The sample was reslurried into 100 ml 80° C. DI $H_2O$; filtered and washed 2 times with 100 ml 80° C. DI $H_2O$; dried at 110° C. and then calcined 4 hours at 150° C.

To an eppendorf tube, 0.007 g of Example 7 was added. One vial of Sigma IEF Mix 3.6-9.3 Isoelectric Focusing Marker (catalog # I-3018) was dissolved into 250 µl 0.14 M NaCl+0.02 M PBS pH=7.2 and then added to the eppendorf tube. The sample was labeled Example 7 high salt.

To a second eppendorf tube, 0.007 g of Example 8 was added. One vial of Sigma IEF Mix 3.6-9.3 Isoelectric Focusing Marker (catalog # I-3018) was dissolved into 250 µl 0.14 M NaCl+0.02 M PBS pH=7.2 and then added to the eppendorf tube. This sample was labeled Example 8 high salt.

To a third eppendorf tube, 0.007 g of Example 7 was added. One vial of Sigma IEF Mix 3.6-9.3 Isoelectric Focusing Marker (catalog # I-3018) was dissolved into 250 ul 0.02 M PBS pH=7.4 and then added to the eppendorf tube. This sample was labeled Example 7 low salt.

To a fourth eppendorf tube, 0.007 g of Example 8 was added. One vial of Sigma IEF Mix 3.6-9.3 Isoelectric Focusing Marker (catalog # I-3018) was dissolved into 250 µl 0.02 M PBS pH=7.4 and then added to the eppendorf tube. This sample was labeled Example 8 low salt.

To a fifth eppendorf tube, one vial of Sigma IEF Mix 3.6-9.3 Isoelectric Focusing Marker (catalog # I-3018) was dissolved into 250 ul DI $H_2O$ and then added to the eppendorf tube. This sample was labeled protein mixture standard.

Figure 4:
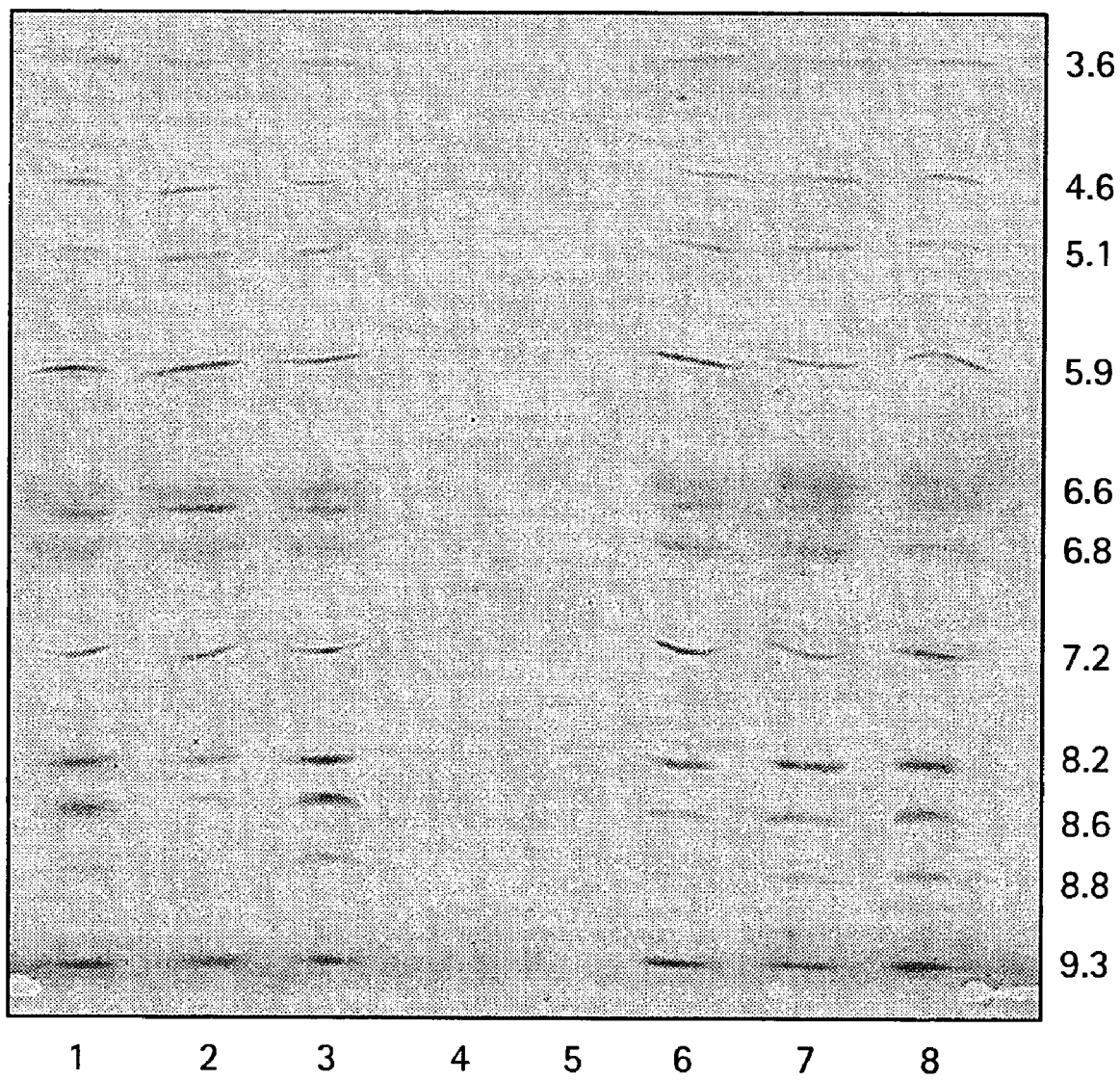
FIG. 4 shows the results of Examples 6–8 and is illustrative of the invention.

All samples were stirred end over end for 1 hour. All samples were then subjected 3-9 Isoelectric Focussing Gel Electrophoresis on a Pharmacia PhastGel unit. The results are shown in FIG. 4.

| Lane | Description |
|------|-------------|
| 1, 8 | protein mixture standard |
|  | Example 7 high salt |
|  | Example 8 high salt |
|  | Example 7 low salt |
|  | Example 8 low salt |

The results of this experiment clearly show the advantage of Example 8, one of the embodiments of this invention, for rejecting nonspecific adsorption to the silica surface, in that all of the protein bands are present, see Lanes 3 and 7, under both "high salt" and "low salt" conditions.

Characterization of Example 8

The surface composition of this invention was characterized by analyses described below.

Figure 5:
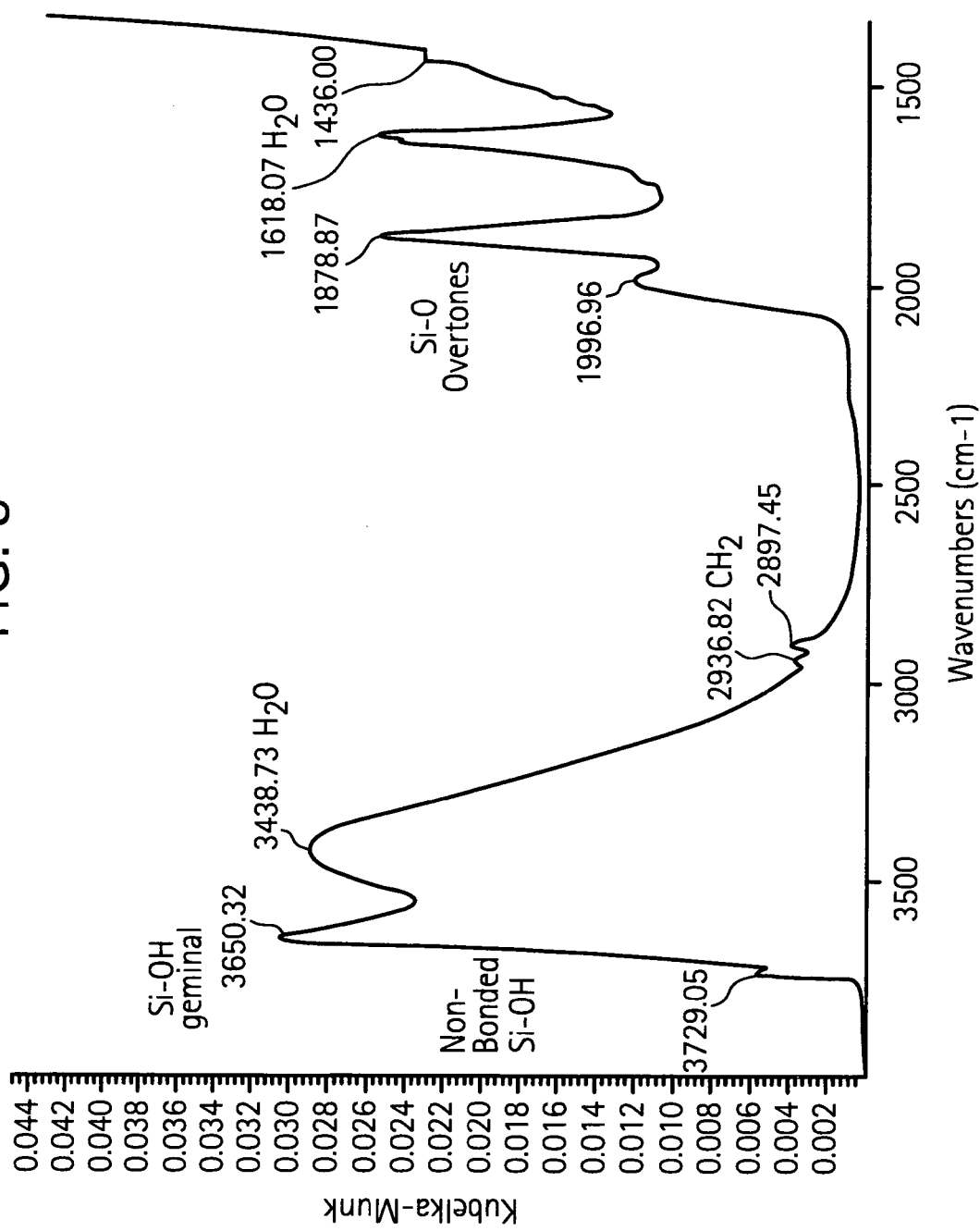
FIGS. 5–8 contain results from analyses conducted to characterize a particular embodiment of the invention (Example 8), with FIG. 5 showing the diffuse reflectance IR spectrum of Example 8, FIG. 6 showing the same spectrum for the composition prepared in Example 7 for comparison, FIG. 7 showing the MAS $Si^{29}$ NMR spectrum of Example 8, and FIG. 8 showing the X-ray photoelectron spectrum, XPS, of Example 8.
Figure 6:
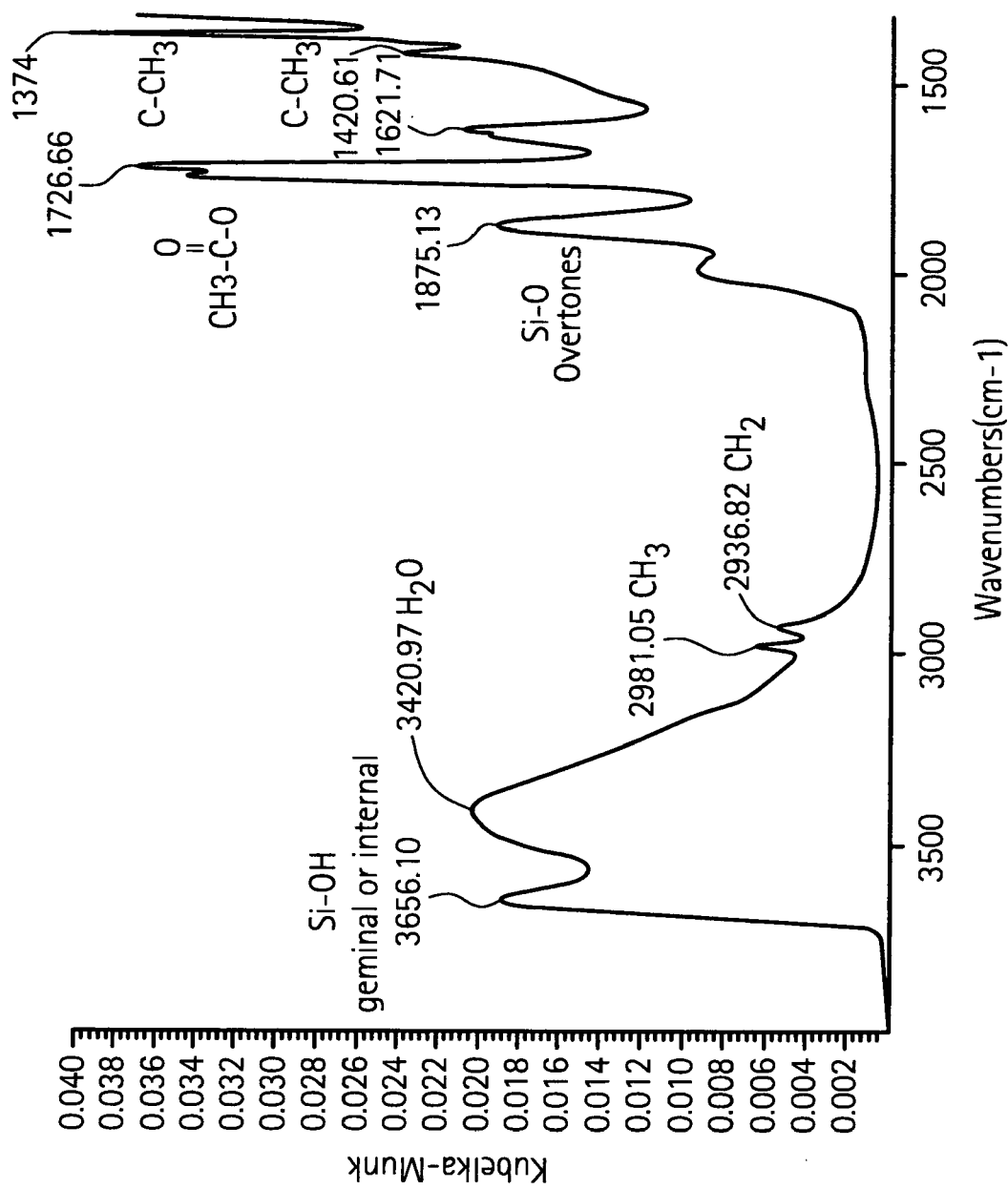

FIG. 5 shows the diffuse reflectance infrared spectrum of Example 8, which had a surface composition comprising —$CH_2OH$ groups, from 1400–4000 $cm^{-1}$. The infrared data were acquired on a Nicolet Magna 550 using a Spectra-Tech diffuse reflectance accessory. The samples were diluted 1:20 in KBr with 512 scans collected at 4 $cm^{-1}$ resolution. The peaks at 2937 and 2897 $cm^{-1}$ clearly show the presence of the —$CH_2$ groups. The bands for the —OH resonances are buried under the broad peak at 3483 $cm^{-1}$. For comparison, FIG. 6 shows the spectrum of Example 7, with a surface composition comprising —$CH_2OCOCH_3$ groups. New resonances occurred at 1726, 1421, and 1374 cm$^{-1}$ which are characteristic resonances associated with the acetoxy groups.

Figure 7:
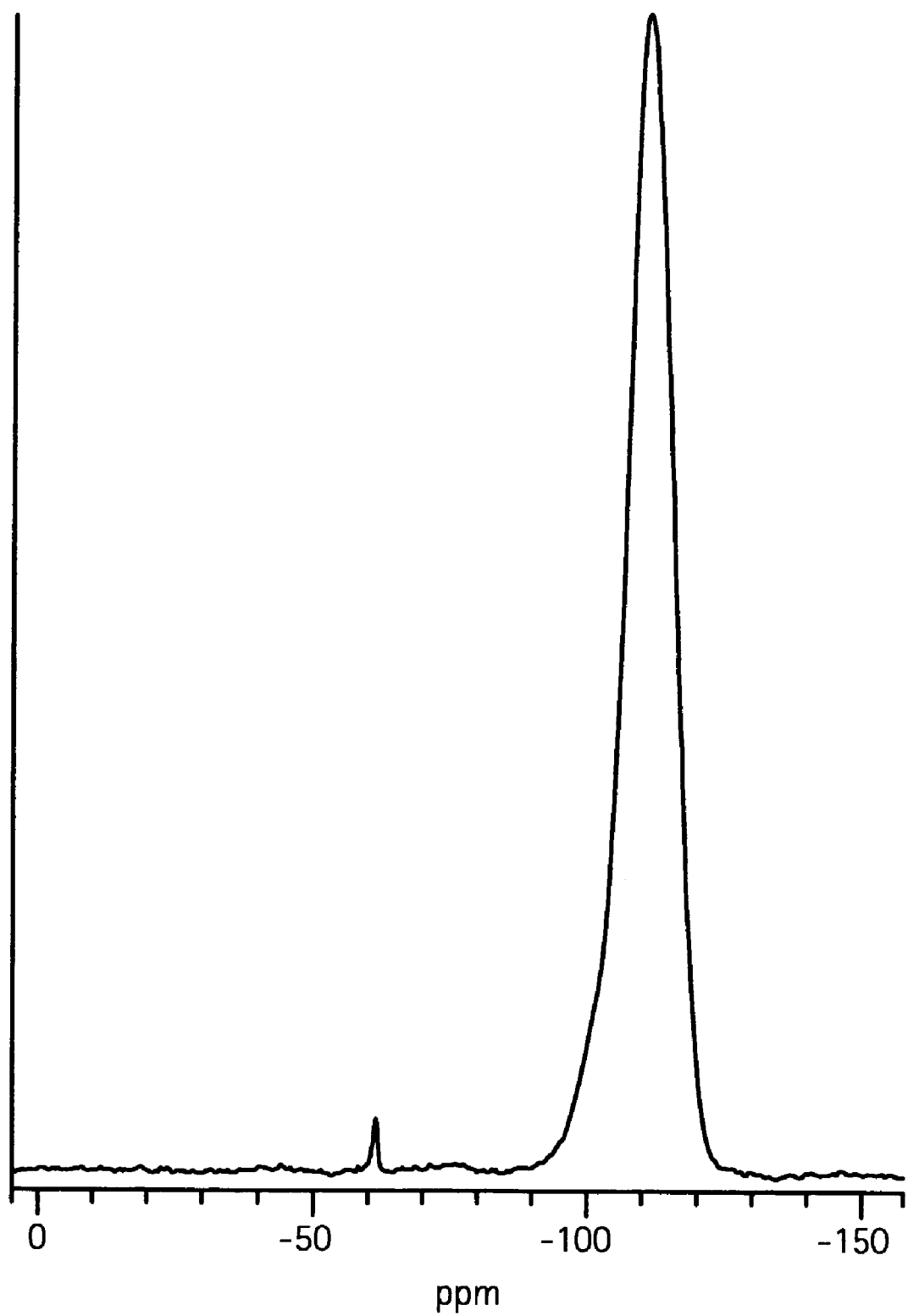

FIG. 7 shows the MAS Si$^{29}$ NMR spectrum of Example 8. A single-pulse $^{29}$Si nuclear magnetic resonance experiment was performed on a Chemagnetics CMX 200 operating at a resonance frequency of 39.76 MHz. The sample was packed in a 14 mm pencil-style rotor. A pulse length of 4 μs corresponding to a 22 degree pulse was utilized along with a relaxation delay of 60 s. The clear resonance at −62 ppm has been identified as O$_3$Si—CH$_x$—, see Vicic, D., and Maciel, J. Am. Chem. Soc. 105 (1983), pg. 3767–3776.

Figure 8:
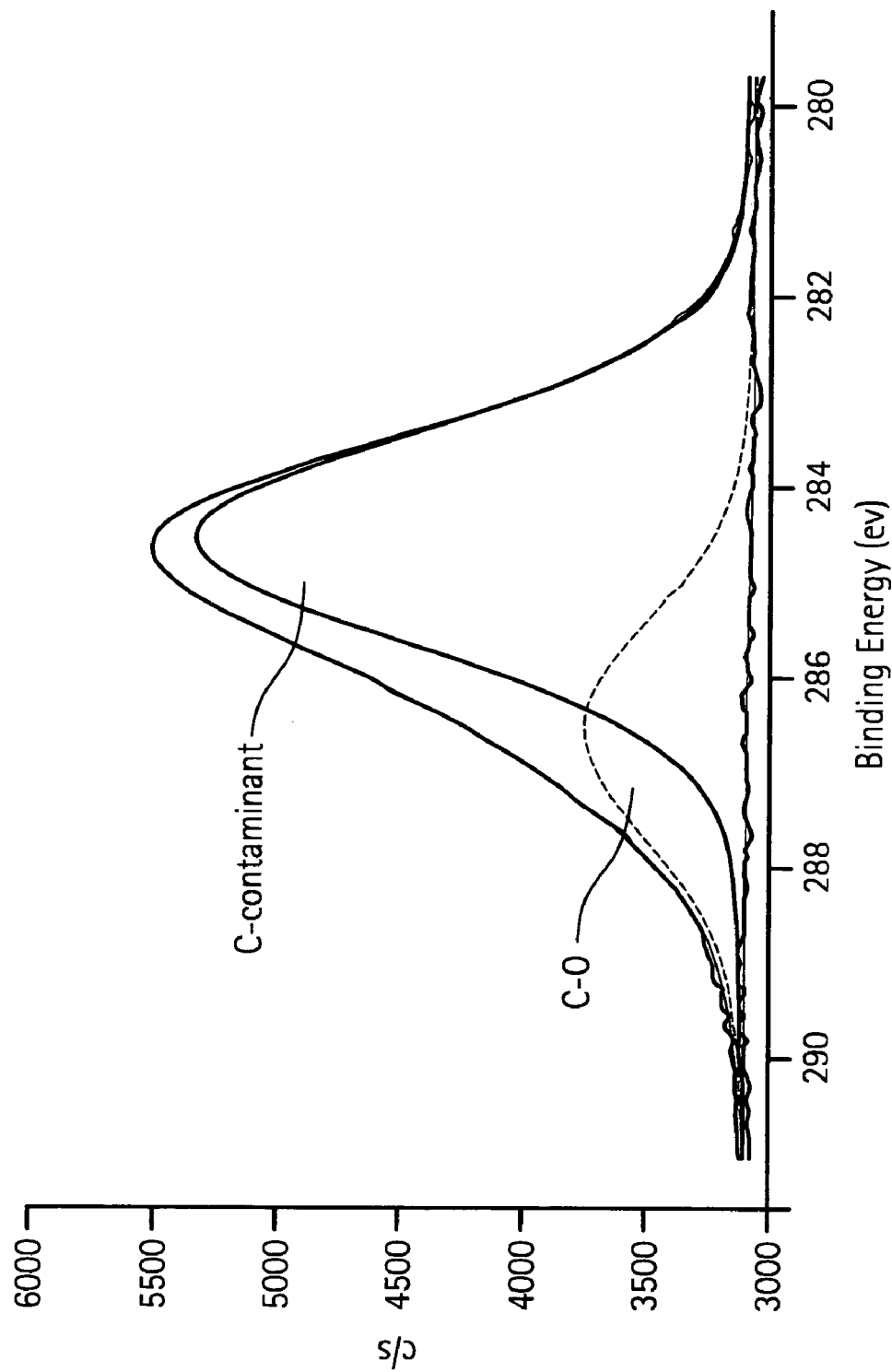
Figure 9:
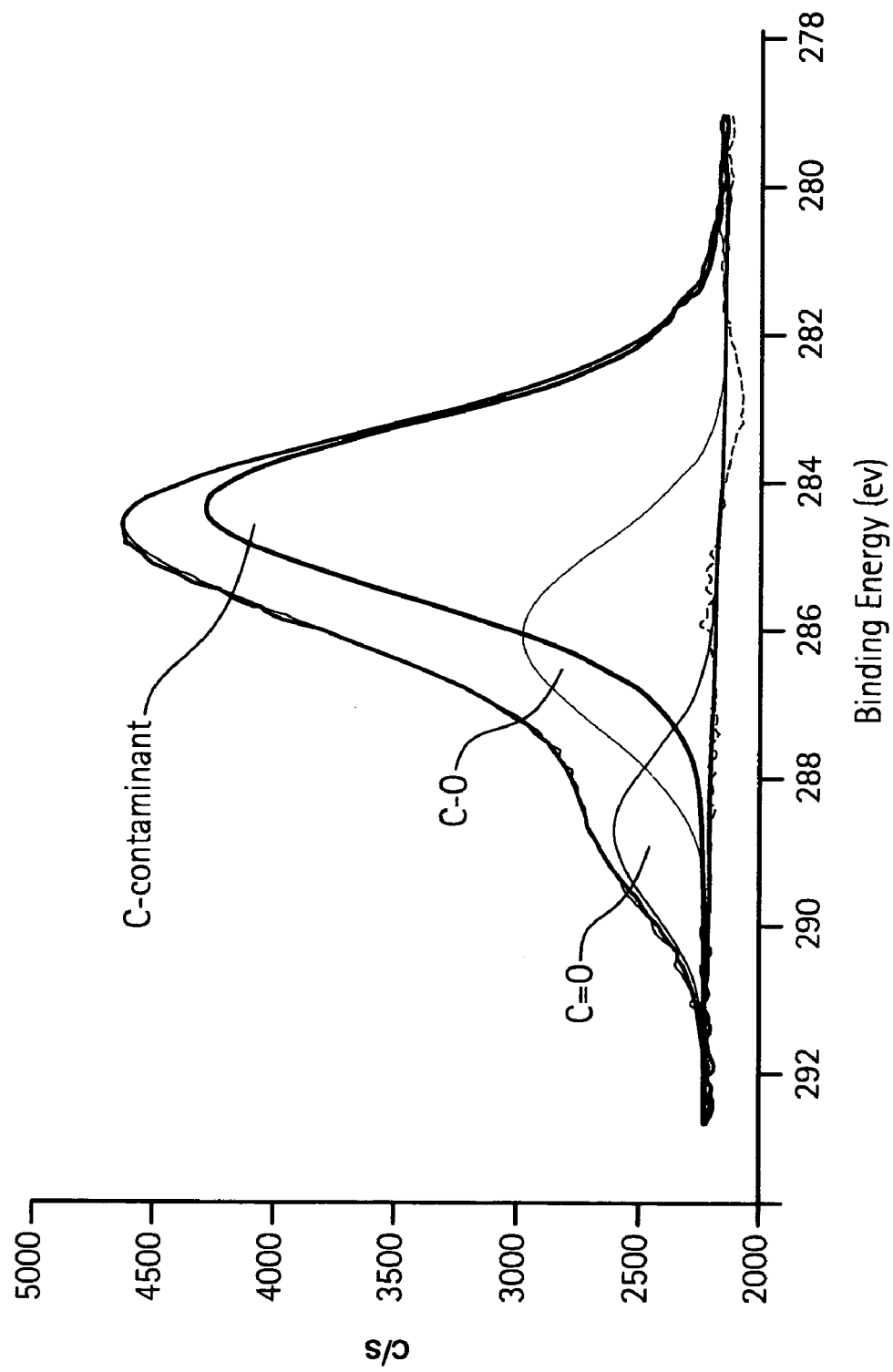
FIG. 9 shows the XPS spectrum of Example 7.

FIG. 8 shows the x-ray photoelectron spectrum of Example 8. The sample was mounted on a sample stub with double-sided tape and a 2 hour carbon, oxygen, and silicon scan was conducted. The spectrum was fit to two peaks which were identified as contaminant C, 284.7 eV, and a alcohol C atom, 286.7 eV, see "Handbook of X-ray Photoelectron Spectroscopy", Moulder, J. F., Sticke, W. F., Sobol, P. E., and Bomben, K. D., Perkin-Elmer Corp, Eden Prairie, Minn., 1992. For comparison the XPS spectrum of Example 7 is shown in FIG. 9. In this case, a peak at 289 eV associated with the carboxyl carbon was also observed. These studies indicate that the surface composition of Example 8, one of the embodiments of this invention, comprised methylhydroxy groups, —CH$_2$OH, e.g., an R$_{10}$ as defined herein.

The concentration of R$_{10}$ groups (—CH$_2$OH) on the product of Example 8 was 2.01 groups/nm$^2$ and was calculated from the surface area of the silica support (72 m$^2$/g) carbon content (1.907%) of the final product. The surface area was measured using conventional BET surface area methodologies and the carbon content (% by weight) was measured using a model C-144 LECO Carbon Analyzer.

EXAMPLE 9

Attachment of Binding Moiety and Illustration of Reduced Non-Specific Binding when Using the Invention 842 g toluene and 3.11 g 3-aminopropyltriethoxysilane were added to a 2000 ml round bottom flask. Then, 200 g of Grace Davison XWP 500 Å silica that was calcined 2 hours at 200° C. was added to the round bottom flask, followed by the addition of 15 boiling chips. The round bottom flask was put in a heating mantle and attached condenser. The heating mantle was attached to the top of an orbital shaker, which was operated at a speed of 115 rpm. N$_2$ was passed through the round bottom flask and condenser to remove air during the entire reaction. The sample was heated to boiling (~110° C.) for 4 hours. The sample was filtered and washed with 2×200 ml toluene, dried at 115° C. and then calcined 2 hours at 150° C. This sample was labeled Intermediary A. The concentration of the resulting —CH$_3$H$_6$NH$_2$ groups was calculated to be 0.54 and was based on the surface area (BET) of the support (88 m$^2$/g), carbon content (LECO) of the intermediary (0.321%) and nitrogen content (0.11%). The nitrogen content (in weight %) was determined on a Carlo Erba NA 1500 Analyzer and using methods based on a modified Dumas method, using an oxygen-containing atmosphere and thermal conducting detection. See ASTM D5373 (for coal) and ASTM 5291.

800 ml 1 M NaCl was mixed with the Intermediary A in a beaker and stirred with a magnetic stirrer. The initial pH was 4.79 1 M HCl was added dropwise until pH became 2. The pH was held at 2.0 for 15 minutes. The sample was filtered and washed with 5×200 ml DI H$_2$O, dried at 115° C. and then calcined 2 hours at 200° C. This sample was labeled Intermediary B.

680 gr toluene and 177.25 gr acetoxymethyltriethoxysilane were mixed with Intermediary B in a round bottom flask. 15 boiling chips were put in the round bottom flask, which was placed in a heating mantle and attached condenser. The heating mantle was attached to the top of an orbital shaker operating a speed of 115 rpm. N$_2$ was passed through the round bottom flask and condenser to remove air during the entire reaction. The sample was heated to boiling (~110° C.) for 24 hours, filtered, washed with 3×200 ml toluene, dried at 115° C. and then calcined 2 hours at 150° C. This sample was labeled Intermediary C.

900 ml dioxane and 100 ml 0.1 M H$_2$SO$_4$ were mixed with Intermediary C in a round bottom flask. 15 boiling chips were put in the round bottom flask, which was placed in a heating mantle and attached condenser. The heating mantle was attached to the top of an orbital shaker operating at a speed of 115 rpm. N$_2$ was passed through the round bottom flask and condenser to remove air for the entire reaction. The sample was heated to boiling (~100° C.) for 4 hours, filtered, washed with 2×200 ml toluene, dried at 115° C. and then calcined 2 hours at 150° C. This sample was labeled Intermediary D. The concentration of R$_{10}$ groups (—CH$_2$OH) of this product was 5.65 and was measured by calculating the carbon content of Intermediary D and then subtracting the amount of carbon attributable to the C$_3$H$_6$NH$_2$ groups, and then marking the calculation made in Example 8. When doing so, the concentration of the C$_3$H$_6$NH$_2$ groups was calculated to be 0.39 and is less than that calculated from data on Intermediary A before conducting the chemistry to attach the R$_{10}$ group. Without being held to a particular theory, it is believed the slight variation in nitrogen content (0.11 vs. 0.08) is due to standard deviation or possibly due to slight leaching of C$_3$H$_6$NH$_2$ groups when creating the R$_{10}$ groups.

20.75 g Intermediary D and 400 ml coupling buffer (0.1 M Na$_2$PO$_4$+0.15 M NaCl; pH=7.0) were mixed in a 1000 ml beaker and stirred for 5 minutes. The sample was filtered to form a moist cake, which was put in a 1000 ml beaker and then 587.66 g 50 wt. % gluteraldehyde and 5.91 g NaCNBH$_3$ were added to the beaker. The sample was stirred for 4 hours, filtered, washed with 400 ml coupling buffer and reslurried in 400 ml coupling buffer to obtain a new sample, which was filtered, washed with 400 ml coupling buffer and reslurried in 400 ml coupling buffer 2 more times. The re-washed and reslurried sample was filtered and then washed with 400 ml coupling buffer. This sample was labeled Intermediary E.

75.44 g coupling buffer and 24.56 g Protein A from Repligen at a concentration of 50 g Protein A per liter were added to a 250 ml round bottom flask. 2.52 g NaCNBH$_3$ and Intermediary E were added to the flask and mixed on a shaker for 4 hours. The sample was filtered and washed 4× with 100 ml coupling buffer. Then 75.44 g coupling buffer, 2.52 g NaCNBH$_3$ and 0.44 g ethanolamine were added to the 250 ml round bottom flask, and then mixed on a shaker for 4 hours. The sample was filtered and washed 4× with 100 ml coupling buffer. The sample was placed in 20% ethanol and stored at 4° C. This sample was labeled Example 9. From LECO Carbon, it was determined that Example 9 was 34.67 mg Protein A per g silica.

A 0.66×2 cm I.D. affinity column packed with silica having —Si—CH$_2$OH directly attached was first equilibrated with 20 mM phosphate buffer, pH 7.4. A 5 ml feed sample of 0.5 mg/ml rabbit polyclonal IgG in supernatant of

Figure 10:
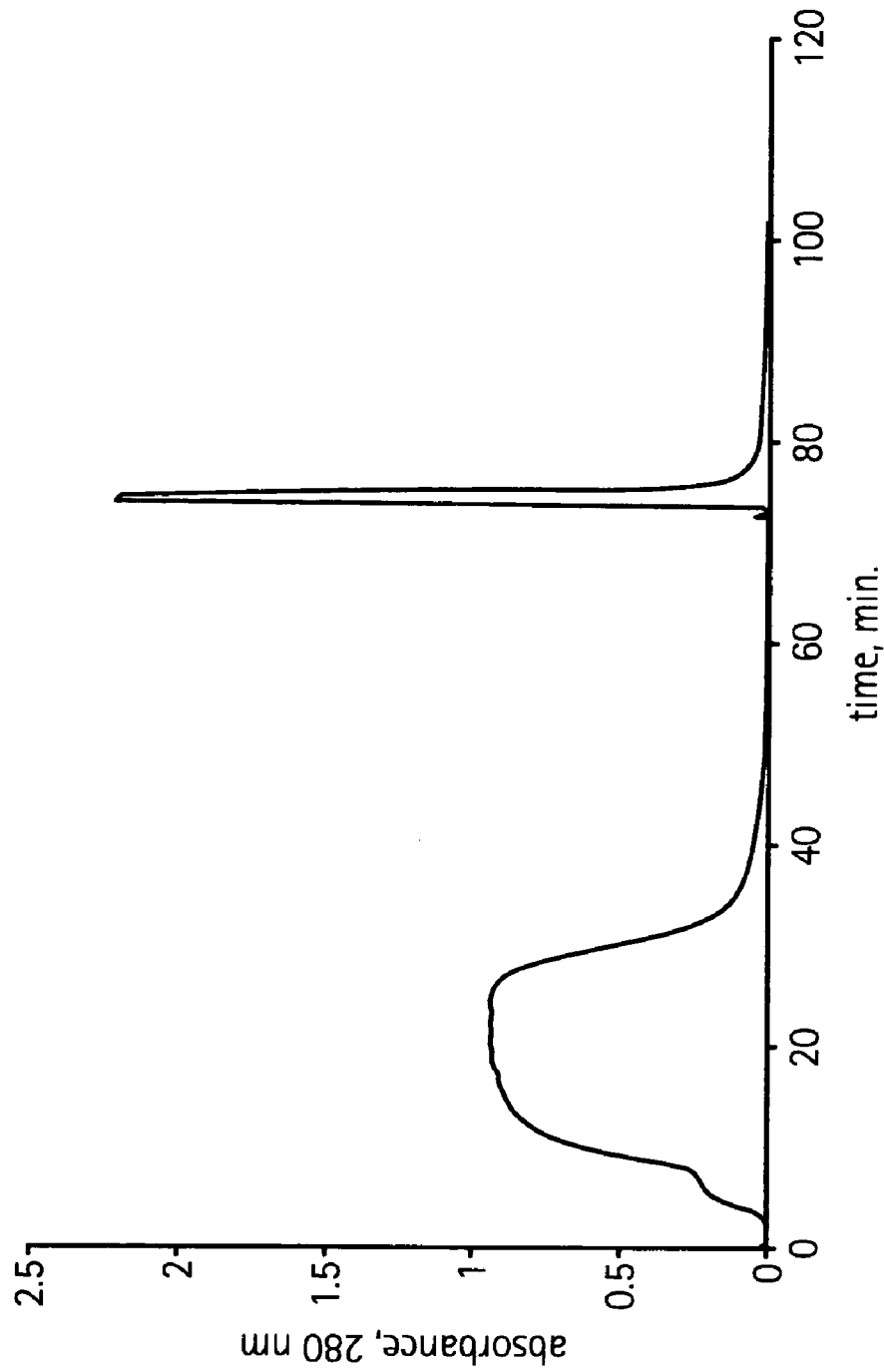
FIG. 10 shows the chromatogram of the loading, wash and elution from a column prepared in Example 9 using the invention after attachment of binding moiety.

*Teredinobacter turnirae* broth was loaded onto the column. The affinity column was then washed with the phosphate buffer until the UV absorbance at 280 nm returned to baseline. The IgG was eluted from the affinity column with 0.1 M acetic acid, pH3.0 at a flow rate of 1 ml/min (see the narrow peak in FIG. 9). FIG. 10 shows the chromatogram of the loading, wash and elution from the affinity column by monitoring the absorbance at 280 nm.

Figure 11:
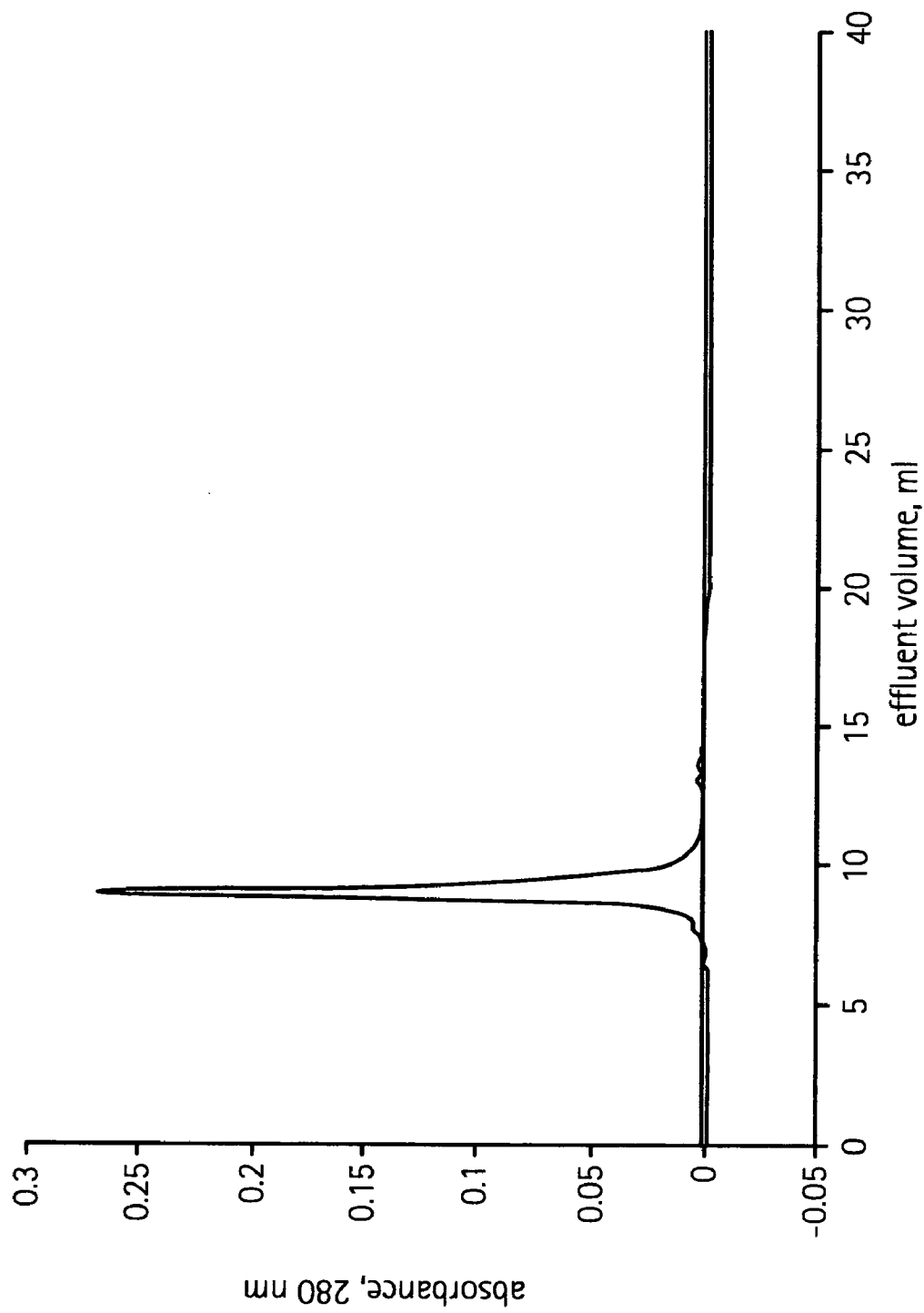
FIG. 11 depicts the absorbance at 280 nm of the effluent from the size exclusion chromatography of purified rabbit polyclonal IgG obtained from the eluent of the affinity chromatography conducted in Example 9.
Figure 12:
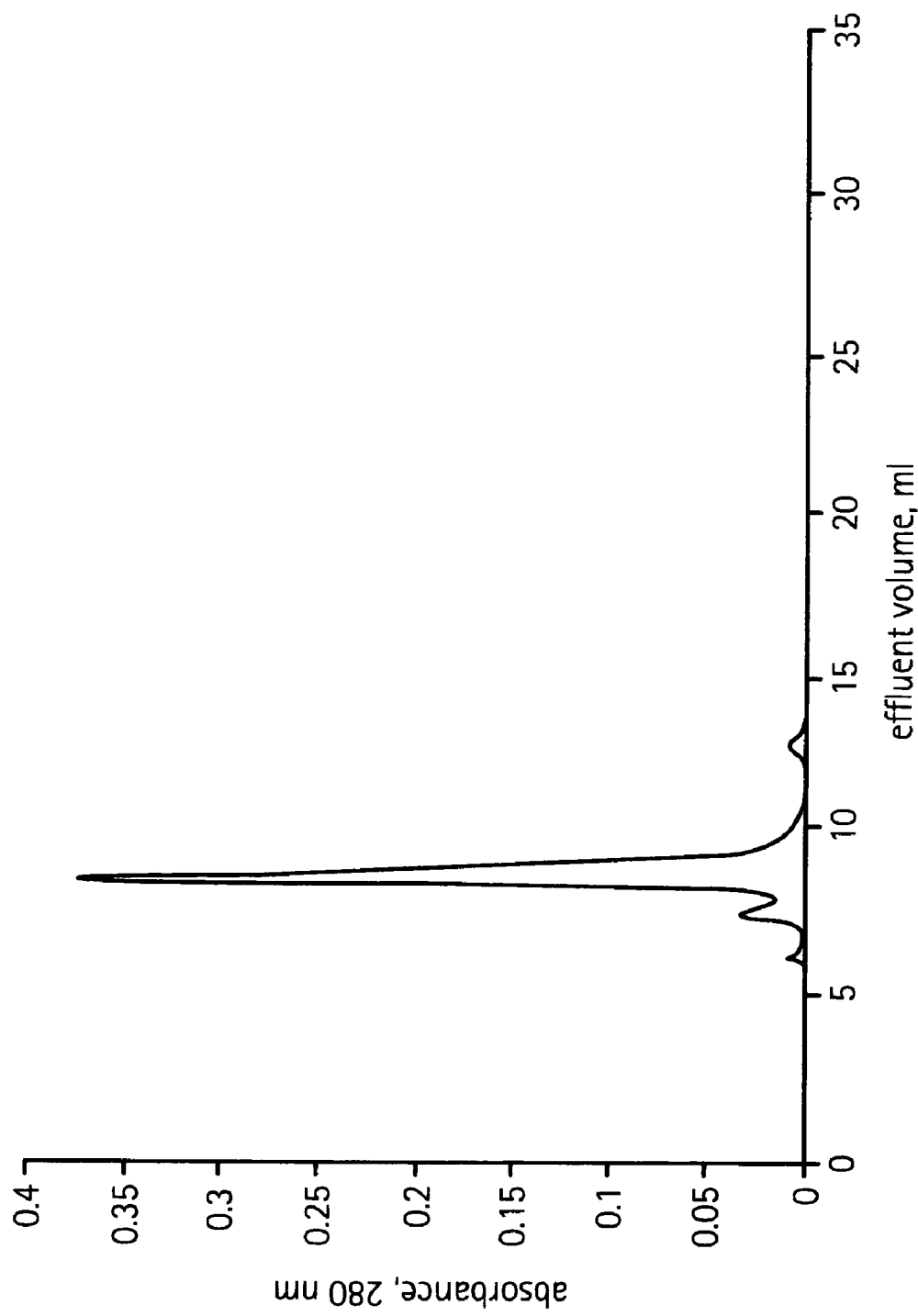
FIG. 12 depicts the absorbance at 280 nm of the effluent from the size exclusion chromatography of the starting rabbit polyclonal IgG that was spiked into a cell broth in Example 9.

100 μL purified IgG from the eluent of the affinity purification shown in FIG. 10 was injected onto a size exclusion chromatography column, which was eluted with an elution buffer of 0.1M $Na_2SO_4$ and 0.05M $NaH_2PO_4$, pH 5, at a flow rate of 1 ml/min. The $A_{280}$ profile of the eluent from the size exclusion chromatography column was depicted in FIG. 11, which shows a single peak of the IgG with very little impurity from the cell broth. By comparison, FIG. 12 shows the size exclusion chromatogram, using the same conditions, of the starting rabbit polyclonal IgG that was spiked into the cell broth. Based on a comparison of FIGS. 11 and 12, it was clear that the IgG purified from the cell broth using Example 9 (FIG. 11) was more pure than the starting IgG (FIG. 12). Thus, FIGS. 11 and 12 show that non-selective binding to the silica media was minimized with the solid of this invention.

BIBLIOGRAPHY

Abercrombie, D. M. et al. *Affinity Chromatography* (eds. Rickwood, D. & Hames, B. D.) (IRL Press, Washington, D.C., 1983).

Argos, P. et al. *Methods in Enzymology* (ed. Deutscher, M. P.) (Academic Press, San Deigo, Calif., 1990).

Gagnon, P. *Purification Tools for Monoclonal Antibodies* (Validated Biosystems, Tuscon, 1996).

Hermanson, G. T., Mallia, A. K. & Smith, P. K. *Immobilized Affinity Ligand Techniques* (Academic Press, Inc., San Diego, 1992).

Mohan, S. B. et al. *Affinity Separations A Practical Approach* (eds. Rickwood, D. & Hames, B. D.) (IRL Press, Oxford, 1997).

Scopes, R. K. *Protein Purification—Principles and Practice* (ed. Cantor, C. R.) (Springer, New York, 1994).

Wheelwright, S. M. *Protein Purification Design and Scale up of Downstream Processing* (John Wiley & Sons, Inc., New York, 1991).

Wilson, R. C. et al. *Protein Purification from Molecular Mechanisms to Large-Scale Processes* (ed. Comstock, M. J.) (The American Chemical Society, Washington, D.C., 1990).

Weetall, "Covalent Coupling Methods for Inorganic Support Materials", in *Methods in Enzymology*, vol. XLIV, edited by K. Mosbach, pp. 134–148, 1976.

The invention claimed is:

1. A solid comprising (i) inorganic substance, (ii) moiety $R_{10}$ covalently bonded to a metal atom on at least one surface of said inorganic substance and (iii) at least one linker, wherein said inorganic substance is inorganic oxide, and said $R_{10}$ is selected from —$CH_2OH$, $CH(OH_2)$, —CH(OH)$CH_3$, —$CH_2CH_2OH$, —C(OH$_2$)CH$_3$, —$CH_2CH(OH_2)$ and CH(OH)$CH_2(OH)$.

2. The solid of claim 1, wherein said at least one linker is optionally substituted bivalent chemical group.

3. The solid of claim 2, wherein the optionally substituted chemical group is hydrocarbyl comprising n —R— groups, with n being the number of —R— groups and n is an integer of at least 2, with n−1 —R— groups optionally replaced with —O—, —S—, carbonyl, thiocarbonyl, —OC(O)—, —C(O)O—, —SC(O)—, —C(O)S—, —OC(S)—, —C(S)O—, —C(S)S—, —SC(S)—, —N($R_4$)—, —N($R_4$)C(O)—, —C(O)N($R_4$)—, —C($R_5$)=N—, —N=C($R_5$)—, —C($R_5$)=NO—, —ON=C($R_5$)—, —P—, —P(OH)O—, arylene, substituted arylene, cycloalkylene, substituted cycloalkylene, cycloalkenylene, substituted cycloalkenylene, bivalent heterocyclyl or substituted heterocyclyl, where $R_4$ and $R_5$ independently being H, alkyl, substituted alkyl, cycloalkyl, substituted cycloalkyl, alkenyl, substituted alkenyl, cycloalkenyl, substituted cycloalkenyl, alkynyl, substituted alkynyl, cycloalkynyl, substituted cycloalkynyl, aryl, substituted aryl, aralkyl or substituted aralkyl.

4. The solid of claim 1, wherein said at least one linker is bivalent optionally substituted chemical group of about 1 to about 30 atoms in length measured from the terminus of said group to the inorganic substance, wherein the chemical group comprises at least one —R— group, with said —R— group being a member selected from the group consisting of —$CH_2$—, —C($R_1$)H—, —C($R_2$)=C($R_3$)— and —C≡C—, where $R_1$, $R_2$ and $R_3$ independently being H, alkyl, substituted alkyl, cycloalkyl, substituted cycloalkyl, alkenyl, substituted alkenyl, cycloalkenyl, substituted cycloalkenyl, alkynyl, substituted alkynyl, cycloalkynyl, substituted cycloalkynyl, aryl, substituted aryl, aralkyl or substituted aralkyl, said —R— group optionally replaced with —O—, —S—, carbonyl, thiocarbonyl, —OC(O)—, —C(O)O—, —SC(O)—, —C(O)S—, —OC(S)—, —C(S)O—, —C(S)S—, —SC(S)—, —N($R_4$)—, —N($R_4$)C(O)—, —C(O)N($R_4$)—, —C($R_5$)=N—, —N=C($R_5$)—, —C($R_5$)=NO—, —ON=C($R_5$)—, —P—, —P(OH)O—, arylene, substituted arylene, cycloalkylene, substituted cycloalkylene, cycloalkenylene, substituted cycloalkenylene, bivalent heterocyclyl or substituted heterocyclyl, where $R_4$ and $R_5$ independently being H, alkyl, substituted alkyl, cycloalkyl, substituted cycloalkyl, alkenyl, substituted alkenyl, cycloalkenyl, substituted cycloalkenyl, alkynyl, substituted alkynyl, cycloalkynyl, substituted cycloalkynyl, aryl, substituted aryl, aralkyl or substituted aralkyl.

5. The solid of claim 1, wherein said at least one linker is attached to the inorganic substance via an ether, thioether, ester, thioester, carbonate, carbamate, phosphate, phosphonate, phosphoester, phosphoramidate, amine, amide, imide, urea, thiourea, sulfonamide, sulfoxide, sulfone, disulfide, oxime, O-acyl oxime, O-carbamoyl oxime, O-acyloxyalkyl oxime, O-acyloxyalkyloxy oxime, O-oximinophosphate, O-oximinophosphonate, O-oximinophosphoramidate or C=C linkage.

6. The solid of claim 1, wherein said at least one linker is formed from cyanogen bromide, a N-hydroxy succinimide ester, carbonyl diimidazole, reductive amination, 2-fluoro-1-methyl-pyridinium toluene-4-sulfonate activation, 1-ethyl-3-(3-dimethylpropyl)carbodiimide mediated amide bond formation, tosyl chloride, tresyl chloride, divinylsulfone, azlactone, cyanuric chloride, iodoacetyl or bromoacetyl activation, maleimide, pyridyl disulfide, an epoxy compound, 2-iminothiolane 5,5-dithio-bis-(2-nitrobenzoic acid), hydrazide, diazonium or Mannich condensation.

7. The solid of claim 1, comprising about 1 to about 10 $R_{10}$ moieties per $nm^2$ solid.

8. The solid of claim 7, wherein said inorganic substance is silica and $R_{10}$ is —$CH_2OH$.

* * * * *